US006465968B1

(12) United States Patent
Sendai

(10) Patent No.: US 6,465,968 B1
(45) Date of Patent: Oct. 15, 2002

(54) METHOD AND APPARATUS FOR DISPLAYING FLUORESCENCE INFORMATION

(75) Inventor: Tomonari Sendai, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 13 days.

(21) Appl. No.: 09/703,674

(22) Filed: Nov. 2, 2000

(30) Foreign Application Priority Data

Nov. 2, 1999 (JP) .......................................... 11-312942
Nov. 2, 1999 (JP) .......................................... 11-312943

(51) Int. Cl.⁷ ................................................. G09G 3/10
(52) U.S. Cl. .................... 315/169.3; 315/149; 315/224; 315/362; 600/160; 600/178
(58) Field of Search ................................. 600/109, 160, 600/178, 310, 317, 342, 475, 476, 478; 315/149, 169.3, 224, 307, 362, 291

(56) References Cited

U.S. PATENT DOCUMENTS 4,995,396 A * 2/1991 Inaba et al. .................... 348/65
5,827,190 A * 10/1998 Palcic et al. ................. 600/109
6,055,451 A * 4/2000 Bambot et al. ............ 250/341.3
6,095,982 A * 8/2000 Richards-Kortum et al. ..... 356/301
6,293,911 B1 * 9/2001 Imaizumi et al. ........... 600/160

OTHER PUBLICATIONS

Lam, S. et al, "Fluorescence Imaging of Early Lung Cancer", IEEE Engineering in Medicine and Biology Society, vol. 12, No. 3, 1990.

* cited by examiner

*Primary Examiner*—Haissa Philogene
(74) *Attorney, Agent, or Firm*—Sughrue Mion, PLLC

(57) ABSTRACT

Excitation light is irradiated to a measuring site in a living body, the excitation light causing the measuring site to produce fluorescence. Light intensity of fluorescence components of the fluorescence produced by the measuring site, which fluorescence components have wavelengths falling within a predetermined wavelength region containing 480 nm, is detected. Also, light intensity of fluorescence components of the fluorescence produced by the measuring site, which fluorescence components have wavelengths falling within a predetermined wavelength region containing either one of 630 nm and 700 nm, is detected. Information in accordance with a ratio between the two detected light intensities is displayed.

14 Claims, 11 Drawing Sheets

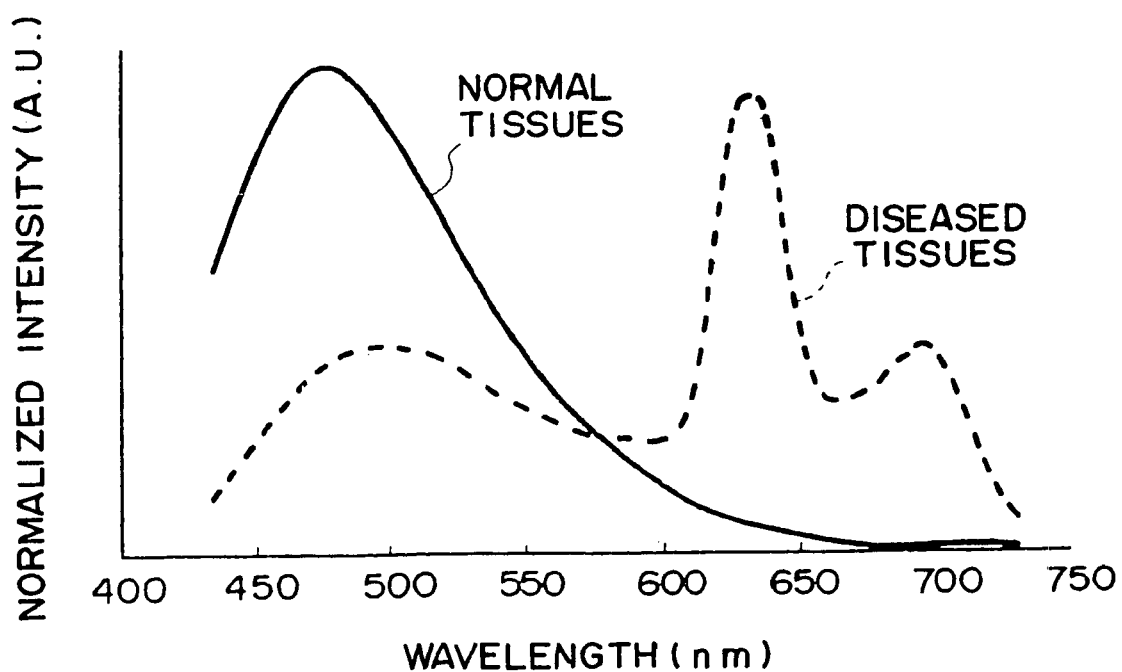
F I G. 6

F I G . 11
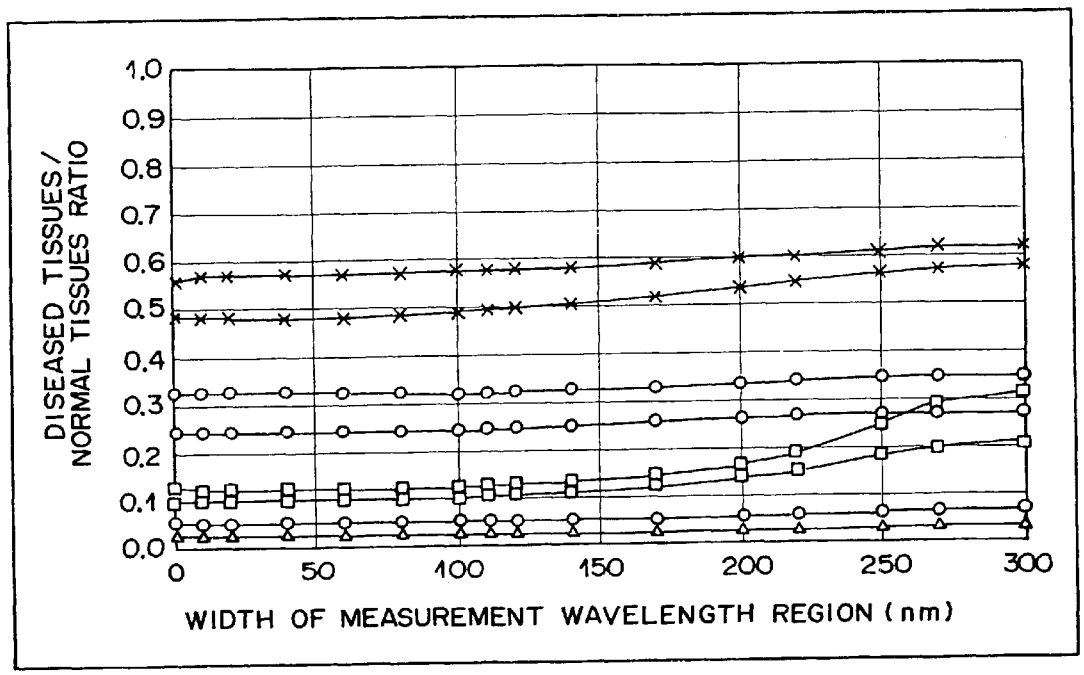

METHOD AND APPARATUS FOR DISPLAYING FLUORESCENCE INFORMATION

BACKGROUND OF THE INVENTION

1. Field of the Invention

This invention relates to a method and apparatus for displaying fluorescence information, wherein excitation light is irradiated to a region of interest in a living body, intrinsic fluorescence produced by an intrinsic dye in the living body is detected, and information in accordance with characteristics of the intrinsic fluorescence is displayed.

2. Description of the Related Art

There have heretofore been proposed fluorescence information displaying techniques utilizing characteristics such that, in cases where excitation light having wavelengths falling within an excitation wavelength range for an intrinsic dye in a living body is irradiated to the living body, an intensity of fluorescence produced by the intrinsic dye in the living body varies for normal tissues and diseased tissues. With the proposed fluorescence information displaying techniques, excitation light having predetermined wavelengths is irradiated to a region of interest in a living body, the fluorescence produced by an intrinsic dye in the living body is detected, and the location and the infiltration range of diseased tissues are displayed as a fluorescence image.

Ordinarily, when excitation light is irradiated to a region of interest in a living body, the fluorescence having a high intensity is produced by normal tissues, and the fluorescence having a low intensity is produced by diseased tissues. Therefore, by measurement of the fluorescence intensity, a judgment as to the state of a disease is capable of being made.

Basically, apparatuses for displaying fluorescence information comprise excitation light irradiating means for irradiating excitation light, which has wavelengths falling within an excitation wavelength range for an intrinsic dye in a living body, to the living body, imaging means for detecting fluorescence produced by the intrinsic dye in the living body and forming a fluorescence image of the living body, and image displaying means for receiving the output from the imaging means and displaying the fluorescence image. In many cases, the apparatuses for displaying fluorescence information take on the form built in endoscopes, which are inserted into the body cavities, colposcopes, operating microscopes, or the like.

However, the aforesaid apparatuses for displaying fluorescence information have the problems described below. Specifically, since a region in a living body has protrusions and recesses, the distance between the light source of the excitation light irradiating means and the region of interest in the living body is not uniform. Therefore, ordinarily, the irradiance of the excitation light at the living body portion, which is exposed to the excitation light, is non-uniform. The intensity of fluorescence is approximately in proportion to the irradiance of the excitation light, and the irradiance of the excitation light at the portion, which is exposed to the excitation light, is in inverse proportion to the square of the distance between the light source of the excitation light irradiating means and the portion, which is exposed to the excitation light. Accordingly, the problems occur in that diseased tissues, which are located close to the light source, produce the fluorescence having a higher intensity than the intensity of the fluorescence produced by normal tissues, which are located remote from the light source. The problems also occur in that the intensity of the fluorescence from normal tissues, which are located at a position inclined with respect to the excitation light, becomes markedly low. Thus if the irradiance of the excitation light is non-uniform, the intensity of the fluorescence will vary in accordance with the level of the irradiance of the excitation light, and therefore an error will often be made in the judgment of the state of a disease.

A fluorescence imaging technique has been proposed in, for example, "Fluorescence Imaging of Early Lung Cancer," Annual International Conference of the IEEE Engineering in Medicine and Biology Society, Vol. 12, No. 3, 1990. With the proposed technique, the fluorescence, which is produced by an intrinsic dye in an region of interest in a living body when the region of interest is exposed to excitation light, is separated into an intensity of the green wavelength region (hereinbelow referred to as the "green region intensity G") and an intensity of the red wavelength region (hereinbelow referred to as the "red region intensity R"). An image operation is then performed in accordance with division of the red region intensity R and the green region intensity G by each other, and the results of the division are displayed. The proposed technique utilizes the findings in that the spectrum of the fluorescence produced by normal tissues is different from the spectrum of the fluorescence produced by diseased tissues. Specifically, when the spectrum of the fluorescence, which is produced by the intrinsic dye at normal tissues in the living body, and the spectrum of the fluorescence, which is produced by the intrinsic dye at diseased tissues in the living body, are compared with each other, in particular, the intensity of the green region of the spectrum obtained from the diseased tissues is markedly lower than the intensity of the green region of the spectrum obtained from the normal tissues. Therefore, the degree of reduction in the intensity of the green region intensity G of the fluorescence, which is produced from the diseased tissues, as compared with the intensity of the green region intensity G of the fluorescence produced from the normal tissues, is markedly higher than the degree of reduction in the intensity of the red region intensity R of the fluorescence, which is produced from the diseased tissues, as compared with the intensity of the red region intensity R of the fluorescence produced from the normal tissues. Therefore, only the fluorescence from the diseased tissues can be specifically extracted by the division of R/G and can be displayed as an image.

Specifically, with the proposed technique, the term of the fluorescence intensity depending upon the distance between the excitation light source and the region of interest in the living body and the distance between the region of interest in the living body and the fluorescence receiving means is canceled, and information reflecting only the difference in fluorescence spectrum pattern is obtained.

However, heretofore, research has not been conducted sufficiently with respect to a combination of detection wavelengths, at which the difference between the pattern of a fluorescence spectrum obtained from normal tissues and the pattern of a fluorescence spectrum obtained from diseased tissues occurs markedly. Therefore, there have been the problems in that a desirable combination of detection wavelengths cannot be presented with numerical values.

SUMMARY OF THE INVENTION

The primary object of the present invention is to provide a method of displaying fluorescence information, wherein fluorescence components having two different wavelengths are extracted from fluorescence, the two different wavelengths having been specified with numerical values as an appropriate combination of detection wavelengths, at which a difference between a pattern of a fluorescence spectrum obtained from normal tissues and a pattern of a fluorescence spectrum obtained from diseased tissues occurs markedly, light intensities of the extracted fluorescence components are detected, and information in accordance with a ratio between the light intensities of the extracted fluorescence components is displayed with a high reliability.

Another object of the present invention is to provide a method of displaying fluorescence information, wherein fluorescence components having wavelengths falling within a certain wavelength region are extracted from fluorescence, the certain wavelength region having been specified with numerical values as an appropriate detection wavelength region, at which a difference between a fluorescence intensity of fluorescence produced from normal tissues and a fluorescence intensity of fluorescence produced from diseased tissues occurs markedly, a light intensity of the extracted fluorescence components is detected, and information in accordance with the detected light intensity is displayed with a high reliability.

The specific object of the present invention is to provide an apparatus for carrying out the method of displaying fluorescence information.

The present invention provides a first method of displaying fluorescence information, comprising the steps of:

i) irradiating excitation light to a measuring site in a living body, the excitation light causing the measuring site to produce fluorescence, ii) detecting light intensity of fluorescence components of the fluorescence produced by the measuring site, which fluorescence components have wavelengths falling within a predetermined wavelength region containing 480 nm, iii) detecting light intensity of fluorescence components of the fluorescence produced by the measuring site, which fluorescence components have wavelengths falling within a predetermined wavelength region containing either one of 630 nm and 700 nm, and iv) displaying information in accordance with a ratio between the two detected light intensities.

The present invention also provides a first apparatus for displaying fluorescence information, comprising:

i) excitation light irradiating means for irradiating excitation light to a measuring site in a living body, the excitation light causing the measuring site to produce fluorescence, ii) first fluorescence intensity detecting means for detecting light intensity of fluorescence components of the fluorescence produced by the measuring site, which fluorescence components have wavelengths falling within a predetermined wavelength region containing 480 nm, iii) second fluorescence intensity detecting means for detecting light intensity of fluorescence components of the fluorescence produced by the measuring site, which fluorescence components have wavelengths falling within a predetermined wavelength region containing either one of 630 nm and 700 nm, and iv) displaying means for displaying information in accordance with a ratio between the light intensity, which has been detected by the first fluorescence intensity detecting means, and the light intensity, which has been detected by the second fluorescence intensity detecting means.

The first apparatus for displaying fluorescence information in accordance with the present invention should preferably be modified such that the first fluorescence intensity detecting means comprises:

first wavelength selecting means for selecting the fluorescence components of the fluorescence produced by the measuring site, which fluorescence components have wavelengths falling within the predetermined wavelength region containing 480 nm, and first light intensity detecting means for detecting the light intensity of the fluorescence components having been selected by the first wavelength selecting means, and the second fluorescence intensity detecting means comprises:

second wavelength selecting means for selecting the fluorescence components of the fluorescence produced by the measuring site, which fluorescence components have wavelengths falling within the predetermined wavelength region containing either one of 630 nm and 700 nm, and second light intensity detecting means for detecting the light intensity of the fluorescence components having been selected by the second wavelength selecting means.

Also, the first apparatus for displaying fluorescence information in accordance with the present invention should more preferably be modified such that the first wavelength selecting means selects the fluorescence components of the fluorescence produced by the measuring site, which fluorescence components have wavelengths falling within the predetermined wavelength region of 480 nm±at most 70 nm, and the second wavelength selecting means selects the fluorescence components of the fluorescence produced by the measuring site, which fluorescence components have wavelengths falling within the predetermined wavelength region of either one of 630 nm±at most 70 nm and 700 nm±at most 70 nm.

Further, in the first apparatus for displaying fluorescence information in accordance with the present invention, the excitation light should preferably have wavelengths falling within the range of 380 nm to 420 nm, which range is apart from the characteristic peak light intensity of the fluorescence produced from normal tissues of the living body. Furthermore, in the first apparatus for displaying fluorescence information in accordance with the present invention, the excitation light irradiating means should preferably be a GaN type of semiconductor laser.

The first apparatus for displaying fluorescence information in accordance with the present invention may be constituted so as to two-dimensionally detect a fluorescence image. Alternatively, the first apparatus for displaying fluorescence information in accordance with the present invention may be constituted so as to detect the fluorescence intensity with respect to each point at a site in the living body.

Also, in the first apparatus for displaying fluorescence information in accordance with the present invention, by way of example, each of the first wavelength selecting means and the second wavelength selecting means may be constituted so as to extract the fluorescence components, which have wavelengths falling within the predetermined wavelength region, with a dichroic mirror, or the like. Alternatively, each of the first wavelength selecting means and the second wavelength selecting means may be constituted so as to extract the fluorescence components, which have wavelengths falling within the predetermined wavelength region, in a time division mode by changing over an optical filter, or the like. As another alternative, in cases where a fluorescence image is to be detected two-dimensionally, each of the first wavelength selecting means and the second wavelength selecting means may be constituted so as to extract the fluorescence components, which have wavelengths falling within the predetermined wavelength region, by utilizing-a mosaic filter formed by connecting optical filters with one another in a mosaic pattern.

Further, in the first apparatus for displaying fluorescence information in accordance with the present invention, the displaying means may employ one of various displaying techniques. For example, the displaying means may be constituted so as to display the ratio between the light intensity of the fluorescence components, which have wavelengths falling within the predetermined wavelength region containing 480 nm, and the light intensity of the fluorescence components, which have wavelengths falling within the predetermined wavelength region containing either one of 630 nm and 700 nm, on a monitor, with a printer, or the like. Alternatively, the displaying means may be constituted so as to alter the tint or the luminance of the displayed color in accordance with the ratio between the two light intensities.

The present invention further provides a second method of displaying fluorescence information, comprising the steps of:
i) irradiating excitation light to a measuring site in a living body, the excitation light causing the measuring site to produce fluorescence,
ii) detecting light intensity B of fluorescence components of the fluorescence produced by the measuring site, which fluorescence components have wavelengths falling within a wavelength region of 480 nm±at most 70 nm and at least containing 450 nm to 480 nm, and
iii) displaying information in accordance with the light intensity B.

The present invention still further provides a third method of displaying fluorescence information, comprising the steps of:
i) irradiating excitation light to a measuring site in a living body, the excitation light causing the measuring site to produce fluorescence,
ii) detecting light intensity W of fluorescence components of the fluorescence produced by the measuring site, which fluorescence components have wavelengths falling within an entire measurement wavelength region,
iii) detecting at least one light intensity selected from among:
light intensity B' of fluorescence components of the fluorescence produced by the measuring site, which fluorescence components have wavelengths falling within a wavelength region of 480 nm±at most 70 nm and at least containing 450 nm to 480 nm,
light intensity R1 of fluorescence components of the fluorescence produced by the measuring site, which fluorescence components have wavelengths falling within a wavelength region of 630 nm±at most 70 nm and at least containing 600 nm to 630 nm, and
light intensity R2 of fluorescence components of the fluorescence produced by the measuring site, which fluorescence components have wavelengths falling within a wavelength region of 700 nm±at most 70 nm and at least containing 700 nm to 710 nm, and
iv) displaying information in accordance with a ratio between the at least one selected light intensity and the light intensity W.

The present invention also provides a fourth method of displaying fluorescence information, comprising the steps of:
i) irradiating excitation light to a measuring site in a living body, the excitation light causing the measuring site to produce fluorescence,
ii) detecting light intensity B of fluorescence components of the fluorescence produced by the measuring site, which fluorescence components have wavelengths falling within a wavelength region of 480 nm±at most 70 nm and at least containing 450 nm to 480 nm,
iii) detecting light intensity W of fluorescence components of the fluorescence produced by the measuring site, which fluorescence components have wavelengths falling within an entire measurement wavelength region,
iv) detecting at least one light intensity selected from among:
light intensity B' of fluorescence components of the fluorescence produced by the measuring site, which fluorescence components have wavelengths falling within a wavelength region of 480 nm±at most 70 nm and at least containing 450 nm to 480 nm,
light intensity R1 of fluorescence components of the fluorescence produced by the measuring site, which fluorescence components have wavelengths falling within a wavelength region of 630 nm±at most 70 nm and at least containing 600 nm to 630 nm, and
light intensity R2 of fluorescence components of the fluorescence produced by the measuring site, which fluorescence components have wavelengths falling within a wavelength region of 700 nm±at most 70 nm and at least containing 700 nm to 710 nm, and
v) displaying information in accordance with the light intensity B and a ratio between the at least one light intensity, which is selected from among the light intensities B', R1, and R2, and the light intensity W.

In the third and fourth methods of displaying fluorescence information in accordance with the present invention, in cases where the light intensity B' is detected as the at least one light intensity, the light intensity B' may be the light intensity of the fluorescence components having wavelengths falling within the wavelength region identical with the wavelength region of the fluorescence components, whose light intensity is detected as the light intensity B. Alternatively, the light intensity B' may be the light intensity of the fluorescence components having wavelengths falling within the wavelength region different from the wavelength region of the fluorescence components, whose light intensity is detected as the light intensity B. In the former cases, instead of the light intensity B' being detected besides the light intensity B, the light intensity B may be employed as the light intensity B'. The term "detecting light intensity B' " as used herein also includes the cases where the light intensity B is employed as the light intensity B'.

The present invention further provides a second apparatus for displaying fluorescence information, comprising:
i) excitation light irradiating means for irradiating excitation light to a measuring site in a living body, the excitation light causing the measuring site to produce fluorescence,
ii) first light intensity detecting means for detecting light intensity B of fluorescence components of the fluorescence produced by the measuring site, which fluorescence components have wavelengths falling within a wavelength region of 480 nm±at most 70 nm and at least containing 450 nm to 480 nm, and iii) fluorescence information displaying means for displaying information in accordance with the light intensity B having been detected by the first light intensity detecting means.

The present invention still further provides a third apparatus for displaying fluorescence information, comprising:

i) excitation light irradiating means for irradiating excitation light to a measuring site in a living body, the excitation light causing the measuring site to produce fluorescence, ii) second light intensity detecting means for detecting light intensity W of fluorescence components of the fluorescence produced by the measuring site, which fluorescence components have wavelengths falling within an entire measurement wavelength region, iii) at least one light intensity detecting means selected from among:

third light intensity detecting means for detecting light intensity B' of fluorescence components of the fluorescence produced by the measuring site, which fluorescence components have wavelengths falling within a wavelength region of 480 nm±at most 70 nm and at least containing 450 nm to 480 nm, fourth light intensity detecting means for detecting light intensity R1 of fluorescence components of the fluorescence produced by the measuring site, which fluorescence components have wavelengths falling within a wavelength region of 630 nm±at most 70 nm and at least containing 600 nm to 630 nm, and fifth light intensity detecting means for detecting light intensity R2 of fluorescence components of the fluorescence produced by the measuring site, which fluorescence components have wavelengths falling within a wavelength region of 700 nm±at most 70 nm and at least containing 700 nm to 710 nm, and iv) fluorescence information displaying means for displaying information in accordance with a ratio between the light intensity, which has been detected by the at least one selected light intensity detecting means, and the light intensity W.

The present invention also provides a fourth apparatus for displaying fluorescence information, comprising:

i) excitation light irradiating means for irradiating excitation light to a measuring site in a living body, the excitation light causing the measuring site to produce fluorescence, ii) first light intensity detecting means for detecting light intensity B of fluorescence components of the fluorescence produced by the measuring site, which fluorescence components have wavelengths falling within a wavelength region of 480 nm±at most 70 nm and at least containing 450 nm to 480 nm, iii) second light intensity detecting means for detecting light intensity W of fluorescence components of the fluorescence produced by the measuring site, which fluorescence components have wavelengths falling within an entire measurement wavelength region, iv) at least one light intensity detecting means selected from among:

third light intensity detecting means for detecting light intensity B' of fluorescence components of the fluorescence produced by the measuring site, which fluorescence components have wavelengths falling within a wavelength region of 480 nm±at most 70 nm and at least containing 450 nm to 480 nm, fourth light intensity detecting means for detecting light intensity R1 of fluorescence components of the fluorescence produced by the measuring site, which fluorescence components have wavelengths falling within a wavelength region of 630 nm±at most 70 nm and at least containing 600 nm to 630 nm, and fifth light intensity detecting means for detecting light intensity R2 of fluorescence components of the fluorescence produced by the measuring site, which fluorescence components have wavelengths falling within a wavelength region of 700 nm±at most 70 nm and at least containing 700 nm to 710 nm, and v) fluorescence information displaying means for displaying information in accordance with the light intensity B and a ratio between the light intensity, which has been detected by the at least one selected light intensity detecting means, and the light intensity W.

In the third and fourth apparatuses for displaying fluorescence information in accordance with the present invention, in cases where the third light intensity detecting means is provided as the at least one light intensity detecting means, the third light intensity detecting means may be identical with the first light intensity detecting means. Alternatively, the third light intensity detecting means may be different from the first light intensity detecting means. In the former cases, instead of the third light intensity detecting means being provided besides the first light intensity detecting means, the first light intensity detecting means may be utilized as the third light intensity detecting means. The term "comprising third light intensity detecting means" as used herein also includes the cases where the first light intensity detecting means is utilized as the third light intensity detecting means.

The second, third, and fourth apparatuses for displaying fluorescence information in accordance with the present invention should preferably be modified such that the light intensity detecting means comprises an image sensor for two-dimensionally detecting the fluorescence produced by the measuring site and forming a fluorescence image, and wavelength selecting means for selecting the fluorescence components of the fluorescence produced by the measuring site, which fluorescence components have wavelengths falling within a desired wavelength region.

Also, the second, third, and fourth apparatuses for displaying fluorescence information in accordance with the present invention may be modified such that the light intensity detecting means is provided with fluorescence acquiring means for acquiring the fluorescence, which is produced by a single point at a site in the living body.

Further, in the second, third, and fourth apparatuses for displaying fluorescence information in accordance with the present invention, the excitation light should preferably have wavelengths falling within the range of 380 nm to 420 nm, which range is apart from the characteristic peak light intensity of the fluorescence produced from normal tissues of the living body. Furthermore, in the second, third, and fourth apparatuses for displaying fluorescence information in accordance with the present invention, the excitation light irradiating means should preferably be a GaN type of semiconductor laser.

Furthermore, in the second, third, and fourth apparatuses for displaying fluorescence information in accordance with the present invention, the fluorescence information displaying means may employ one of various displaying techniques. For example, in cases where the light intensity of the fluorescence components of the fluorescence produced by the measuring site, which fluorescence components have wavelengths falling within a predetermined wavelength region containing 480 nm, and the light intensity of the fluorescence components of the fluorescence, which fluorescence components have wavelengths falling within the entire measurement wavelength region, are detected and the information in accordance with the ratio between the two detected light intensities are displayed, the fluorescence information displaying means may be constituted so as to display the ratio between the two detected light intensities on a monitor, with a printer, or the like. Alternatively, the fluorescence information displaying means may be constituted so as to alter the tint or the luminance of the displayed color in accordance with the ratio between the two detected light intensities.

The first method of displaying fluorescence information and the first apparatus for displaying fluorescence information in accordance with the present invention have the effects described below.

When the excitation light is irradiated to living body tissues, the living body tissues are excited by the excitation light and produce the fluorescence having a spectrum illustrated in FIG. 5. It is assumed that the thus produced fluorescence results from superposition of the fluorescence produced by various kinds of intrinsic dyes in the living body, such as FAD, collagen, fibronectin, and porphyrin. FIG. 5 shows typical fluorescence spectra of the fluorescence produced from normal tissues and the fluorescence produced from diseased tissues, which fluorescence spectra have been measured by the inventors.

As illustrated in FIG. 5, the level and the pattern of the spectrum of the fluorescence vary for the normal tissues and the diseased tissues. The level of the fluorescence produced from the normal tissues is high as a whole, and the level of the fluorescence produced from the diseased tissues is low as a whole. The fluorescence spectrum obtained from the normal tissues has a peak spectral intensity at a region in the vicinity of 480 nm, which region is a blue region. The fluorescence spectrum obtained from the diseased tissues has a peak spectral intensity at a region in the vicinity of 630 nm, which region is a red region, and a peak spectral intensity at a region in the vicinity of 700 nm.

FIG. 6 is a graph showing a distribution of ratios of spectral intensities at respective wavelengths of a fluorescence spectrum, which is obtained from normal tissues, to a spectral intensity of an entire measurement wavelength region width, which spectral intensity is taken as 1, and a distribution of ratios of spectral intensities at respective wavelengths of a fluorescence spectrum, which is obtained from diseased tissues, to a spectral intensity of the entire measurement wavelength region width, which spectral intensity is taken as 1. As illustrated in FIG. 6, the distributions of the spectral intensity ratios more clearly manifest the difference between the pattern of the fluorescence spectrum of the fluorescence produced from the normal tissues and the pattern of the fluorescence spectrum of the fluorescence produced from the diseased tissues.

In accordance with FIG. 5 and FIG. 6, the inventors studied about an appropriate combination of detection wavelengths, at which the difference between the pattern of the fluorescence spectrum obtained from the normal tissues and the pattern of the fluorescence spectrum obtained from the diseased tissues occurs markedly.

As a result, it has been found that, in cases where the light intensity at the wavelength region in the vicinity of 480 nm and the light intensity at the wavelength region in the vicinity of 630 nm or in the vicinity of 700 nm are detected, the ratio between the two detected light intensities markedly represents the difference between the pattern of the fluorescence spectrum obtained from the normal tissues and the pattern of the fluorescence spectrum obtained from the diseased tissues.

Specifically, the light intensity at the predetermined wavelength region containing 480 nm, at which a high light intensity is obtained characteristically from the normal tissues, and the light intensity at the predetermined wavelength region containing 630 nm or 700 nm, at which a high light intensity is obtained characteristically from the diseased tissues, are detected from the fluorescence having been detected from the measuring site, whose tissue state is unknown. Also, the information in accordance with the ratio between the two detected light intensities is displayed. In such cases, a person, who sees the displayed information, is capable of presuming whether the tissues at the measuring site are the normal tissues or the diseased tissues.

As described above, with the first method of displaying fluorescence information and the first apparatus for displaying fluorescence information in accordance with the present invention, the excitation light is irradiated to the measuring site in the living body, the excitation light causing the measuring site to produce the fluorescence. Also, the light intensity of the fluorescence components of the fluorescence produced by the measuring site, which fluorescence components have wavelengths falling within the predetermined wavelength region containing 480 nm, is detected. Further, the light intensity of the fluorescence components of the fluorescence produced by the measuring site, which fluorescence components have wavelengths falling within the predetermined wavelength region containing either one of 630 nm and 700 nm. Thereafter, the information in accordance with the ratio between the two detected light intensities is displayed. Therefore, with the first method of displaying fluorescence information and the first apparatus for displaying fluorescence information in accordance with the present invention, the information having enhanced reliability is capable of being displayed.

In the first apparatus for displaying fluorescence information in accordance with the present invention, the first fluorescence intensity detecting means may comprise the first wavelength selecting means for selecting the fluorescence components of the fluorescence produced by the measuring site, which fluorescence components have wavelengths falling within the predetermined wavelength region containing 480 nm, and the first light intensity detecting means for detecting the light intensity of the fluorescence components having been selected by the first wavelength selecting means. Also, the second fluorescence intensity detecting means may comprise the second wavelength selecting means for selecting the fluorescence components of the fluorescence produced by the measuring site, which fluorescence components have wavelengths falling within the predetermined wavelength region containing either one of 630 nm and 700 nm, and the second light intensity detecting means for detecting the light intensity of the fluorescence components having been selected by the second wavelength selecting means. With the thus modified first apparatus for displaying fluorescence information in accordance with the present invention, the light intensity at each of the predetermined wavelength regions is capable of being detected easily.

Also, from the results of analysis made on the fluorescence spectra illustrated in FIG. 5 and FIG. 6, it has been found that, if the width of the predetermined wavelength region containing 480 nm is broader than 480 nm±70 nm, the ratio of the light intensity at the predetermined wavelength region detected from the diseased tissues to the light intensity at the predetermined wavelength region detected from the normal tissues will become high. Further, it has been found that, if the width of the predetermined wavelength region containing 630 nm is broader than 630 nm ±70 nm, or if the width of the predetermined wavelength region containing 700 nm is broader than 700 nm±70 nm, the ratio of the light intensity at the predetermined wavelength region detected from the diseased tissues to the light intensity at the predetermined wavelength region detected from the normal tissues will become low. Therefore, with the first apparatus for displaying fluorescence information in accordance with the present invention, wherein the first wavelength selecting means selects the fluorescence components of the fluorescence produced by the measuring site, which fluorescence components have wavelengths falling within the predetermined wavelength region of 480 nm ±at most 70 nm, and the second wavelength selecting means selects the fluorescence components of the fluorescence produced by the measuring site, which fluorescence components have wavelengths falling within the predetermined wavelength region of either one of 630 nm±at most 70 nm and 700 nm±at most 70 nm, the light intensity ratio having reliability enhanced even further is capable of being obtained.

Further, with the first apparatus for displaying fluorescence information in accordance with the present invention, wherein the excitation light has wavelengths falling within the range of 380 nm to 420 nm that is apart from the region in the vicinity of 480 nm, at which the light intensity of the fluorescence produced from the normal tissues becomes characteristically high, the fluorescence having the fluorescence spectrum of a desirable pattern is capable of being produced, and therefore the reliability of the displayed information is capable of being enhanced. Furthermore, with the first apparatus for displaying fluorescence information in accordance with the present invention, wherein the GaN type of semiconductor laser is employed as the excitation light irradiating means, the size of the apparatus is capable of being kept small, and the cost of the apparatus is capable of being kept low.

The second, third, and fourth methods of displaying fluorescence information and the second, third, and fourth apparatuses for displaying fluorescence information in accordance with the present invention have the effects described below.

As illustrated in FIG. 5, the level and the pattern of the spectrum of the fluorescence vary for the normal tissues and the diseased tissues. The level of the intrinsic fluorescence produced from the normal tissues is high as a whole, and the level of the intrinsic fluorescence produced from the diseased tissues is low as a whole. The fluorescence spectrum obtained from the normal tissues has a peak spectral intensity at a region in the vicinity of 480 nm, which region is the blue region. However, at the region in the vicinity of 480 nm, only slight fluorescence is produced from the diseased tissues. From FIG. 5, it can be found that the wavelengths, at which the difference between the spectral intensity of the fluorescence spectrum obtained from the normal tissues and the spectral intensity of the fluorescence spectrum obtained from the diseased tissues occurs markedly, are the wavelengths in the vicinity of 480 nm, and the wavelength of 480 nm is desirable as the center wavelength of the detection wavelengths.

Also, in experiments made by the inventors and with respect to a plurality of patients, fluorescence spectra of the fluorescence produced from diseased tissues and the fluorescence produced from normal tissues located in the vicinity of the diseased tissues were detected. Thereafter, from each of the fluorescence spectra, light intensities at various measurement wavelength regions having different widths and having their centers at 480 nm were calculated. With respect to each of the widths of the measurement wavelength regions, the ratio of the light intensity of the fluorescence produced from the diseased tissues to the light intensity of the fluorescence produced from the normal tissues was calculated. From the calculations, the results shown in FIG. 11 were obtained.

From the results shown in FIG. 11, it can be found that, in cases where the width of the measurement wavelength region is at most 100 nm, i.e. in cases where the measurement wavelength region is 480 nm at most 50 nm, little change occurs in the ratio of the light intensity of the fluorescence produced from the diseased tissues to the light intensity of the fluorescence produced from the normal tissues. Also, it can be found that, in cases where the width of the measurement wavelength region is 150 nm, the ratio of the light intensity of the fluorescence produced from the diseased tissues to the light intensity of the fluorescence produced from the normal tissues becomes high and close to 1, and the contrast between the fluorescence produced from the normal tissues and the fluorescence produced from the diseased tissues becomes low. Therefore, it can be found desirable to extract the fluorescence components having wavelengths falling within the wavelength region width of at most 140 nm around the wavelength of 480 nm, i.e. the wavelengths falling within the wavelength region of 480 nm±at most 70 nm, at which wavelength region little increase occurs with the ratio of the light intensity of the fluorescence produced from the diseased tissues to the light intensity of the fluorescence produced from the normal tissues.

Further, from the results of experiments, it has been found that the wavelength corresponding to the peak spectral intensity in the fluorescence spectrum often varies slightly for different persons and different measuring sites in a single person, and therefore the light intensity at the wavelength region, which at least contains 450 nm to 480 nm, should be detected.

FIG. 6 shows the distribution of ratios of spectral intensities at respective wavelengths of the fluorescence spectrum, which is obtained from the normal tissues, to the spectral intensity of the entire measurement wavelength region width, which spectral intensity is taken as 1, and the distribution of ratios of spectral intensities at respective wavelengths of the fluorescence spectrum, which is obtained from the diseased tissues, to the spectral intensity of the entire measurement wavelength region width, which spectral intensity is taken as 1. In cases where the ratios of the spectral intensities at respective wavelengths of the fluorescence spectrum to the spectral intensity of the entire measurement wavelength region width are calculated, adverse effects of a difference in measurement conditions, such as a measurement distance, can be eliminated. Therefore, the distributions of the spectral intensity ratios manifest the difference between the pattern of the fluorescence spectrum of the fluorescence produced from the normal tissues and the pattern of the fluorescence spectrum of the fluorescence produced from the diseased tissues. The fluorescence spectrum obtained from the normal tissues has the peak spectral intensity at the region in the vicinity of 480 nm. The fluorescence spectrum obtained from the diseased tissues has the peak spectral intensity at the region in the vicinity of 630 nm, and the peak spectral intensity at the region in the vicinity of 700 nm.

In accordance with FIG. 6, the inventors studied about measurement wavelengths and measurement wavelength region width, at which the difference between the pattern of the fluorescence spectrum obtained from the normal tissues and the pattern of the fluorescence spectrum obtained from the diseased tissues occurs markedly. The study was made in the same manner as that described above and by setting the center wavelengths at 480 nm, 630 nm, and 700 nm. FIG. 12 shows the results obtained from experiments, in which the center wavelength was set at 480 nm, the measurement wavelength region width was set at various different values, the ratio of the light intensity of each measurement wavelength region width to the light intensity of the entire measurement wavelength region width was calculated with respect to each of the fluorescence produced from the normal tissues and the fluorescence produced from the diseased tissues, and the ratio of the thus calculated light intensity ratio for the diseased tissues to the thus calculated light intensity ratio for the normal tissues was calculated.

As a result, from the study made with the spectral intensity ratio distribution, as in the study made with the spectral intensity distribution, in cases where the center wavelength is 480 nm, it has been found desirable to extract the fluorescence components having wavelengths falling within the wavelength region width of at most 140 nm around the wavelength of 480 nm, i.e. the wavelengths falling within the wavelength region of 480 nm±at most 70 nm and at least containing 450 nm to 480 nm, at which wavelength region little increase occurs with the ratio of the light intensity of the fluorescence produced from the diseased tissues to the light intensity of the fluorescence produced from the normal tissues and the contrast between the fluorescence produced from the normal tissues and the fluorescence produced from the diseased tissues does not become low.

Also, though not shown, in cases where the center wavelength is set at 630 nm, it has been found desirable to extract the fluorescence components having wavelengths falling within the wavelength region of 630 nm±at most 70 nm and at least containing 600 nm to 630 nm. Further, in cases where the center wavelength is set at 700 nm, it has been found desirable to extract the fluorescence components having wavelengths falling within the wavelength region of 700 nm±at most 70 nm and at least containing 700 nm to 710 nm.

Specifically, the fluorescence components having the wavelengths falling within the wavelength region described above are extracted from the fluorescence having been detected from the measuring site, whose tissue state is unknown, and the light intensity of the extracted fluorescence components is detected. Also, the information in accordance with the detected light intensity is displayed. In such cases, a person, who sees the displayed information, is capable of accurately presuming whether the tissues at the measuring site are the normal tissues or the diseased tissues.

As described above, with the second method of displaying fluorescence information and the second apparatus for displaying fluorescence information in accordance with the present invention, the excitation light is irradiated to the measuring site in the living body, the excitation light causing the measuring site to produce the fluorescence. Also, the light intensity B of the fluorescence components of the fluorescence produced by the measuring site, which fluorescence components have wavelengths falling within the wavelength region of 480 nm ±at most 70 nm and at least containing 450 nm to 480 nm, is detected. Further, the information in accordance with the light intensity B is displayed. Therefore, with the second method of displaying fluorescence information and the second apparatus for displaying fluorescence information in accordance with the present invention, the information having enhanced reliability is capable of being displayed.

With the third method of displaying fluorescence information and the third apparatus for displaying fluorescence information in accordance with the present invention, the excitation light is irradiated to the measuring site in the living body, the excitation light causing the measuring site to produce the fluorescence. Also, the light intensity W of the fluorescence components of the fluorescence produced by the measuring site, which fluorescence components have wavelengths falling within the entire measurement wavelength region, is detected. Further, at least one light intensity is detected, the at least one light intensity being selected from among the light intensity B' of the fluorescence components of the fluorescence produced by the measuring site, which fluorescence components have wavelengths falling within the wavelength region of 480 nm±at most 70 nm and at least containing 450 nm to 480 nm, the light intensity R1 of the fluorescence components of the fluorescence produced by the measuring site, which fluorescence components have wavelengths falling within the wavelength region of 630 nm ±at most 70 nm and at least containing 600 nm to 630 nm, and the light intensity R2 of the fluorescence components of the fluorescence produced by the measuring site, which fluorescence components have wavelengths falling within the wavelength region of 700 nm±at most 70 nm and at least containing 700 nm to 710 nm. Furthermore, the information in accordance with the ratio between the at least one selected light intensity and the light intensity W is displayed. Therefore, with the third method of displaying fluorescence information and the third apparatus for displaying fluorescence information in accordance with the present invention, adverse effects of fluctuations in spectral intensity due to fluctuations in measurement conditions, such as the measurement distance and the measurement angle, are capable of being reduced, and the information having enhanced reliability, which represents the feature of the spectrum pattern, is capable of being displayed.

With the fourth method of displaying fluorescence information and the fourth apparatus for displaying fluorescence information in accordance with the present invention, the excitation light is irradiated to the measuring site in the living body, the excitation light causing the measuring site to produce the fluorescence. Also, the light intensity B of the fluorescence components of the fluorescence produced by the measuring site, which fluorescence components have wavelengths falling within the wavelength region of 480 nm±at most 70 nm and at least containing 450 nm to 480 nm, is detected. Further, the light intensity W of the fluorescence components of the fluorescence produced by the measuring site, which fluorescence components have wavelengths falling within the entire measurement wavelength region, is detected. Furthermore, at least one light intensity is detected, the at least one light intensity being selected from among the light intensity B' of the fluorescence components of the fluorescence produced by the measuring site, which fluorescence components have wavelengths falling within the wavelength region of 480 nm±at most 70 nm and at least containing 450 nm to 480 nm, the light intensity R1 of the fluorescence components of the fluorescence produced by the measuring site, which fluorescence components have wavelengths falling within the wavelength region of 630 nm ±at most 70 nm and at least containing 600 nm to 630 nm, and the light intensity R2 of the fluorescence components of the fluorescence produced by the measuring site, which fluorescence components have wavelengths falling within the wavelength region of 700 nm±at most 70 nm and at least containing 700 nm to 710 nm. Also, the information in accordance with the light intensity B and the ratio between the at least one light intensity, which is selected from among the light intensities B', R1, and R2, and the light intensity W is displayed. Therefore, with the fourth method of displaying fluorescence information and the fourth apparatus for displaying fluorescence information in accordance with the present invention, the information having enhanced reliability, which represents the characteristics of the spectral intensity and the spectrum pattern, is capable of being displayed.

With the second, third, and fourth apparatuses for displaying fluorescence information in accordance with the present invention, wherein each of the light intensity detecting means is provided with the image sensor for two-dimensionally detecting the fluorescence produced by the measuring site and forming a fluorescence image, the information concerning the fluorescence over a wide range is capable of being displayed quickly.

With the second, third, and fourth apparatuses for displaying fluorescence information in accordance with the present invention, wherein each of the light intensity detecting means is provided with the fluorescence acquiring means for acquiring the fluorescence, which is produced by a single point at a site in the living body, the information concerning the fluorescence produced from a desired point at the site is capable of being displayed.

With the second, third, and fourth apparatuses for displaying fluorescence information in accordance with the present invention, wherein the excitation light has the wavelengths falling within the range of 380 nm to 420 nm that is apart from the region in the vicinity of 480 nm, at which region the light intensity of the fluorescence produced from normal tissues takes the characteristically large value, the fluorescence with the fluorescence spectrum in a desirable pattern is capable of being produced, and the reliability of the displayed information is capable of being enhanced. Furthermore, with the second, third, and fourth apparatuses for displaying fluorescence information in accordance with the present invention, wherein the GaN type of semiconductor laser is employed as the excitation light irradiating means, the size of the apparatus is capable of being kept small, and the cost of the apparatus is capable of being kept low.

BRIEF DESCRIPTION OF THE DRAWINGS

FIG. 6 is a graph showing spectral intensity ratio distributions of fluorescence spectra of fluorescence produced from normal tissues and fluorescence produced from diseased tissues, FIG. 11 is a graph showing relationship between a width of a measurement wavelength region and a ratio of light intensity of fluorescence produced from diseased tissues to light intensity of fluorescence produced from normal tissues.

DESCRIPTION OF THE PREFERRED EMBODIMENTS

The present invention will hereinbelow be described in further detail with reference to the accompanying drawings.

Figure 1:
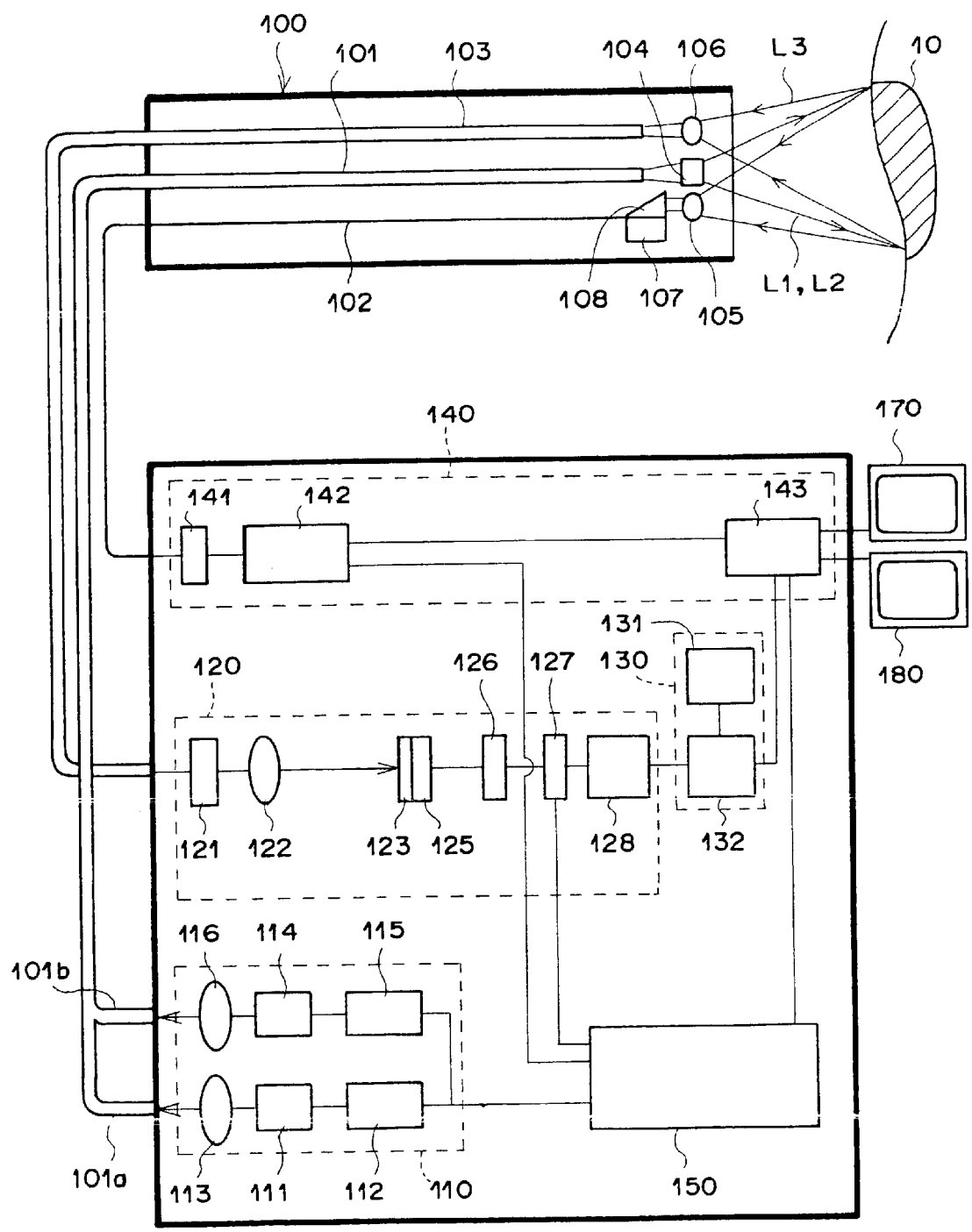
FIG. 1 is a schematic view showing an endoscope system, in which a first embodiment of the apparatus for displaying fluorescence information in accordance with the present invention is employed.

Firstly, an endoscope system, in which a first embodiment of the apparatus for displaying fluorescence information in accordance with the present invention is employed, will be described hereinbelow with reference to FIG. 1 and FIG. 2. FIG. 1 is a schematic view showing the endoscope system, in which the first embodiment of the apparatus for displaying fluorescence information in accordance with the present invention is employed. In the endoscope system, in which the first embodiment of the apparatus for displaying fluorescence information in accordance with the present invention is employed, excitation light is irradiated to a measuring site in a living body, the excitation light causing the measuring site to produce fluorescence. The fluorescence produced from the measuring site is two-dimensionally detected with an image fiber and received by a high-sensitivity image sensor. Also, light intensity B of fluorescence components of the fluorescence, which fluorescence components have wavelengths falling within a wavelength region of 480 nm±70 nm, and light intensity R of fluorescence components of the fluorescence, which fluorescence components have wavelengths falling within a wavelength region of 630 nm±70 nm, are detected. Further, an R-to-B ratio is calculated, and information in accordance with the results of the calculation is displayed.

The endoscope system, in which the first embodiment of the apparatus for displaying fluorescence information in accordance with the present invention is employed, comprises an endoscope 100 to be inserted into a region of a patient, which region is considered as being a diseased part, and an illuminating unit 110 provided with light sources for producing white light, which is used when an ordinary image is to be displayed, and the excitation light, which is used when fluorescence information is to be displayed. The endoscope system also comprises an R-to-B ratio calculating unit 120 for receiving the fluorescence, which is produced from the measuring site in the living body when the measuring site is exposed to the excitation light, and calculating the R-to-B ratio. The endoscope system further comprises a comparison unit 130 for comparing a reference value, which has been stored previously, and the calculated R-to-B ratio with each other and feeding out a signal in accordance with the results of the comparison. The endoscope system still further comprises an image processing unit 140 for performing image processing for displaying the ordinary image and the results of the comparison as visible images. The endoscope system also comprises a controller 150, which is connected to the respective units and controls operation timings. The endoscope system further comprises a monitor 170 for displaying the ordinary image information, which has been obtained from the image processing performed by the image processing unit 140, as a visible image, and a monitor 180 for displaying the results of the comparison, which have been obtained from the image processing performed by the image processing unit 140.

A light guide 101, a CCD cable 102, and an image fiber 103 extend in the endoscope 100 up to a leading end of the endoscope 100. An illuminating lens 104 is located at a leading end of the light guide 101, i.e. at the leading end of the endoscope 100. An objective lens 105 is located at a leading end of the CCD cable 102, i.e. at the leading end of the endoscope 100. The image fiber 103 is constituted of quartz glass fibers, a converging lens 106 is located at a leading end of the image fiber 103. A CCD image sensor 107 is connected to the leading end of the CCD cable 102, and a mirror 108 is mounted on the CCD image sensor 107. The light guide 101 comprises a white light guide 101a, which is constituted of a compound glass fiber, and an excitation light guide 101b, which is constituted of a quartz glass fiber. The white light guide 101a and the excitation light guide 101b are bundled together in a cable-like form to constitute the light guide 101. The white light guide 101a a and the excitation light guide 101b are connected to the illuminating unit 110. A tail end of the CCD cable 102 is connected to the image processing unit 140. A tail end of the image fiber 103 is connected to the R-to-B ratio calculating unit 120.

The illuminating unit 110 comprises a white light source 111 for producing white light L1, which is used when an ordinary image is to be displayed, and an electric power source 112, which is electrically connected to the white light source 111. The illuminating unit 110 also comprises a GaN type of semiconductor laser 114 for producing excitation light L2, which is used when fluorescence information is to be displayed, and an electric power source 115, which is electrically connected to the GaN type of semiconductor laser 114.

The R-to-B ratio calculating unit 120 comprises an excitation light cut-off filter 121 for filtering out light, which has wavelengths in the vicinity of the wavelength of the excitation light L2, from fluorescence L3 having passed through the image fiber 103. The R-to-B ratio calculating unit 120 also comprises a CCD image sensor 125 combined with a mosaic filter 123, which comprises two kinds of optical filters combined with each other in a mosaic-like form. The R-to-B ratio calculating unit 120 further comprises an analog-to-digital converting circuit 126 for digitizing a fluorescence signal, which has been obtained from the CCD image sensor 125. The R-to-B ratio calculating unit 120 still further comprises a fluorescence image memory 127 for storing a fluorescence image signal having been obtained from the analog-to-digital converting circuit 126. The R-to-B ratio calculating unit 120 also comprises R-to-B ratio calculating means 128 for calculating the R-to-B ratio from the fluorescence image signal having been stored in the fluorescence image memory 127.

Figure 2:
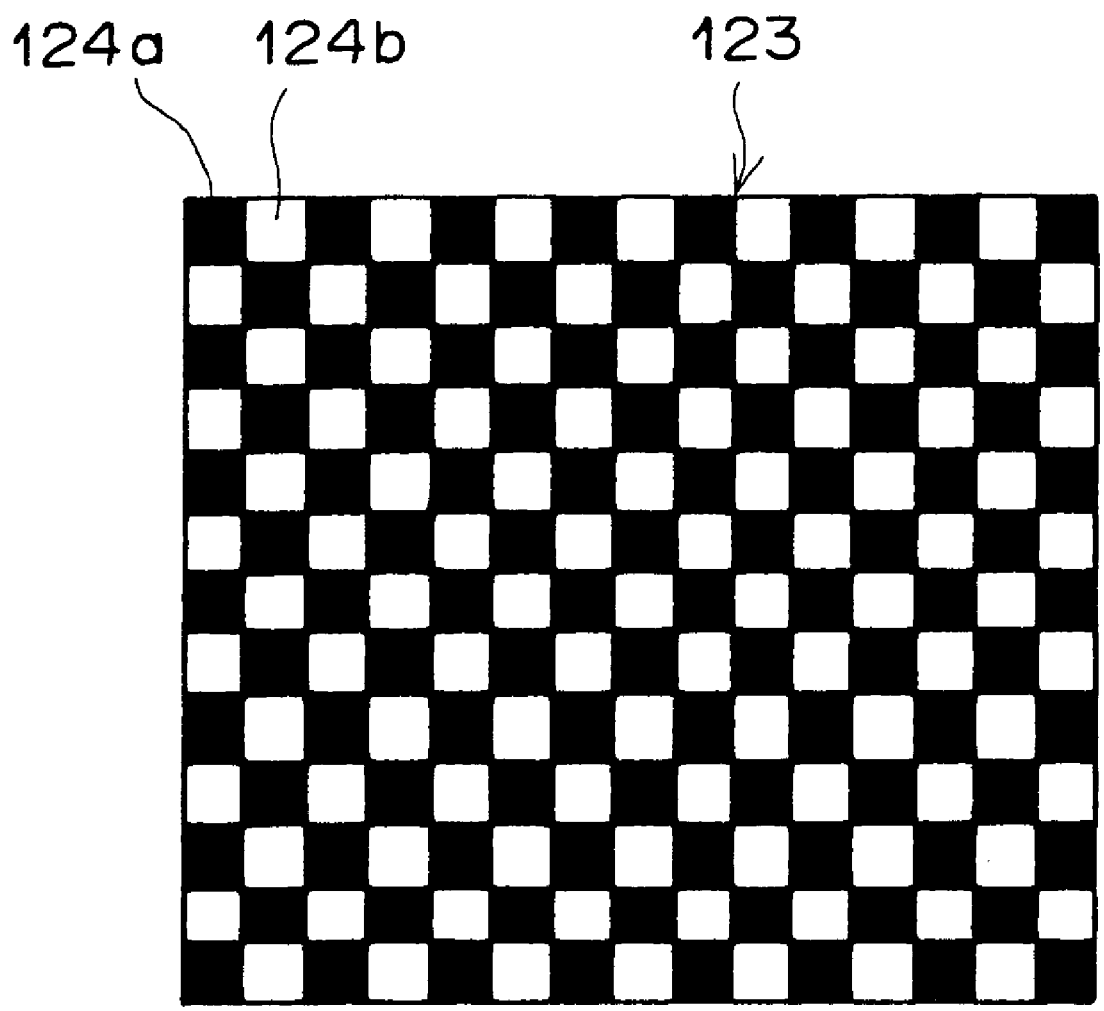
FIG. 2 is a schematic view showing a mosaic filter, which is employed in the first embodiment.

As illustrated in FIG. 2, the mosaic filter 123 is constituted of optical filters 124a, 124a, . . . and optical filters 124b, 124b, . . . The optical filters 124a, 124a, . . . are band-pass filters, which transmit only light having wavelengths falling within a wavelength region of 480 nm±70 nm. The optical filters 124b, 124b, . . . are band-pass filters, which transmit only light having wavelengths falling within a wavelength region of 630 nm±70 nm.

The comparison unit 130 comprises storage means 131 for storing a reference value RE. The comparison unit 130 also comprises comparison means 132 for comparing the R-to-B ratio, which has been calculated by the R-to-B ratio calculating means 128, and the reference value RE, which has been stored in the storage means 131, with each other.

The reference value RE is set in accordance with an R-to-B ratio having been calculated previously with respect to living body tissues, which have been found as being normal tissues or diseased tissues.

The image processing unit 140 comprises an analog-to-digital converting circuit 141 for digitizing an image signal, which has been obtained from the CCD image sensor 107. The image processing unit 140 also comprises an ordinary image memory 142 for storing a digital ordinary image signal, which has been obtained from the analog-to-digital converting circuit 141. The image processing unit 140 further comprises a video signal processing circuit 143 for converting the image signal, which has been received from the ordinary image memory 142, and the results of the comparison, which have been obtained from the comparison means 132, into video signals.

How the endoscope system, in which the first embodiment of the apparatus for displaying fluorescence information in accordance with the present invention is employed, operates will be described hereinbelow. Firstly, how the endoscope system operates when an ordinary image is to be displayed will be described hereinbelow.

When an ordinary image is to be displayed, the electric power source 112 for the white light source 111 is driven in accordance with a control signal fed from the controller 150, and the white light L1 is produced by the white light source 111. The white light L1 passes through a lens 113 and impinges upon the white light guide 101a. The white light L1 is guided through the white light guide 101a to the leading end of the endoscope 100, passes through the illuminating lens 104, and is irradiated to a measuring site 10.

The white light L1 reflected from the measuring site 10 is converged by the objective lens 105 and reflected by the mirror 108, and an image of the reflected white light L1 is formed on the CCD image sensor 107. The image signal obtained from the CCD image sensor 107 is fed into the analog-to-digital converting circuit 141 and converted into the digital ordinary image signal. The digital ordinary image signal is stored in the ordinary image memory 142. The digital ordinary image signal is then fed from the ordinary image memory 142 into the video signal processing circuit 143 and converted into an analog ordinary image signal. The thus obtained analog ordinary image signal is fed into the monitor 170 and used for displaying a visible image on the monitor 170. The series of the operations described above are controlled by the controller 150.

How the endoscope system operates when fluorescence information is to be displayed will be described hereinbelow.

When fluorescence information is to be displayed, the electric power source 115 for the GaN type of semiconductor laser 114 is driven in accordance with a control signal fed from the controller 150, and the excitation light L2 having a wavelength of 410 nm is produced by the GaN type of semiconductor laser 114. The excitation light L2 passes through a lens 116 and impinges upon the excitation light guide 101b. The excitation light L2 is guided through the excitation light guide 101b to the leading end of the endoscope 100, passes through the illuminating lens 104, and is irradiated to the measuring site 10.

When the measuring site 10 is exposed to the excitation light L2, the fluorescence L3 is produced from the measuring site 10. The fluorescence L3 is converged by the converging lens 106 and impinges upon the leading end of the image fiber 103. The fluorescence L3 then passes through the image fiber 103 and impinges upon the excitation light cut-off filter 121.

Thereafter, the fluorescence L3 is converged by a lens 122 and passes through the mosaic filter 123, which is combined with the CCD image sensor 125. The fluorescence L3 is then received by the CCD image sensor 125, and a fluorescence image signal is obtained from the CCD image sensor 125. The fluorescence image signal having been obtained from the CCD image sensor 125 is fed into the analog-to-digital converting circuit 126 and converted into a digital fluorescence image signal. The digital fluorescence image signal having been obtained from the analog-to-digital converting circuit 126 is stored in the fluorescence image memory 127.

At this time, fluorescence image signal components representing fluorescence components of the fluorescence L3, which fluorescence components have passed through the optical filters 124a, 124a, . . . of the mosaic filter 123, and fluorescence image signal components representing fluorescence components of the fluorescence L3, which fluorescence components have passed through the optical filters 124b, 124b, . . . of the mosaic filter 123, are stored in different memory areas of the fluorescence image memory 127. Therefore, the fluorescence image signal components representing the fluorescence components, which have wavelengths falling within the wavelength region of 480 nm±70 nm, and the fluorescence image signal components representing the fluorescence components, which have wavelengths falling within the wavelength region of 630 nm±70 nm, are alternately stored in the memory areas of the fluorescence image memory 127.

The R-to-B ratio calculating means 128 calculates the R-to-B ratio with respect to each area of the measuring site 10 by utilizing the fluorescence image signal components, which have been stored in adjacent areas of the fluorescence image memory 127.

The comparison means 132 compares the R-to-B ratio, which has been calculated by the R-to-B ratio calculating means 128 and with respect to each area of the measuring site 10, and the reference value RE, which has been stored in the storage means 131, with each other.

The results of the comparison are displayed as an image on the monitor 180. In such cases, the display color with respect to the measured area is altered between when the R-to-B ratio is at most equal to the reference value RE and when the R-to-B ratio is higher than the reference value RE. Therefore, the measurer is capable of instantaneously recognize the results of the comparison.

Alternatively, instead of the comparison being made with respect to each pixel, the comparison processing may be made in units of pixels corresponding to binning processing of the CCD image sensor 125. As another alternative, the comparison may be made in units of an arbitrary pixel area, which is desired by the measurer. As a further alternative, the comparison may be made with respect to only an area specified by the measurer. As a still further alternative, pixels may be thinned out, and the comparison may then be made.

In cases where the comparison processing has not been made with respect to a certain area, the display color with respect to the certain area may be set at a predetermined color. In such cases, the area having been subjected to the comparison processing is capable of being displayed clearly. In cases where the pixels has been thinned out and then the comparison has been made, the results of the comparison corresponding to the pixels, which have been removed by the thinning-out process, may be interpolated from the results of the comparison corresponding to the neighboring pixels.

As described above, in the first embodiment, the fluorescence components of the fluorescence L3, which fluorescence components have wavelengths falling within the wavelength region of 480 nm±70 nm, and the fluorescence components of the fluorescence L3, which fluorescence components have wavelengths falling within the wavelength region of 630 nm±70 nm, are extracted from the fluorescence L3, which is produced from the measuring site 10 when the excitation light L2 is irradiated to the measuring site 10.

Also, the light intensity B of the fluorescence components, which have wavelengths falling within the wavelength region of 480 nm±70 nm, and the light intensity R of the fluorescence components, which have wavelengths falling within the wavelength region of 630 nm±70 nm, are detected. Further, the R-to-B ratio is calculated and compared with the reference value RE, and the results of the comparison are displayed. Therefore, with the first embodiment, the information having enhanced reliability is capable of being displayed.

Also, with the first embodiment, wherein the GaN type of semiconductor laser 114, which produces the excitation light L2 having a wavelength of 410 nm, is employed as the excitation light irradiating means, the light intensity of the fluorescence is capable of being detected appropriately. Further, the size of the apparatus for displaying fluorescence information is capable of being kept small, and the cost of the apparatus is capable of being kept low.

As illustrated in FIG. 2, in the first embodiment, the mosaic filter 123 is constituted of the optical filters 124a, 124a, . . . , which transmits only light having wavelengths falling within the wavelength region of 480 nm±70 nm, and the optical filters 124b, 124b, . . . , which transmits only light having wavelengths falling within the wavelength region of 630 nm±70 nm. Alternatively, a mosaic filter, which is constituted of the optical filters 124a, 124a, . . . , the optical filters 124b, 124b, . . . , and blank areas for transmitting light having wavelengths falling within the entire measurement wavelength region, may be located in front of the CCD image sensor 125. In such cases, the CCD image sensor 125 is capable of being utilized for both the detection of the ordinary image and the detection of the fluorescence.

Further, a CCD image sensor combined with the aforesaid mosaic filter, which is constituted of the optical filters 124a, 124a, . . . , the optical filters 124b, 124b, and the blank areas, may be located at the leading end of the endoscope 100. In such cases, the CCD image sensor is capable of being utilized for both the detection of the ordinary image and the detection of the fluorescence.

Furthermore, the comparison is made as to whether the R-to-B ratio is at most equal to the reference value RE or higher than the reference value RE, and the results of the comparison are displayed. Alternatively, the ratio obtained from the division of the light intensities of the two wavelength regions may be directly displayed. As another alternative, each of the light intensities may be displayed with an additive color process, and the ratio between the light intensities may be displayed as a change in tint on the display screen.

Figure 3:
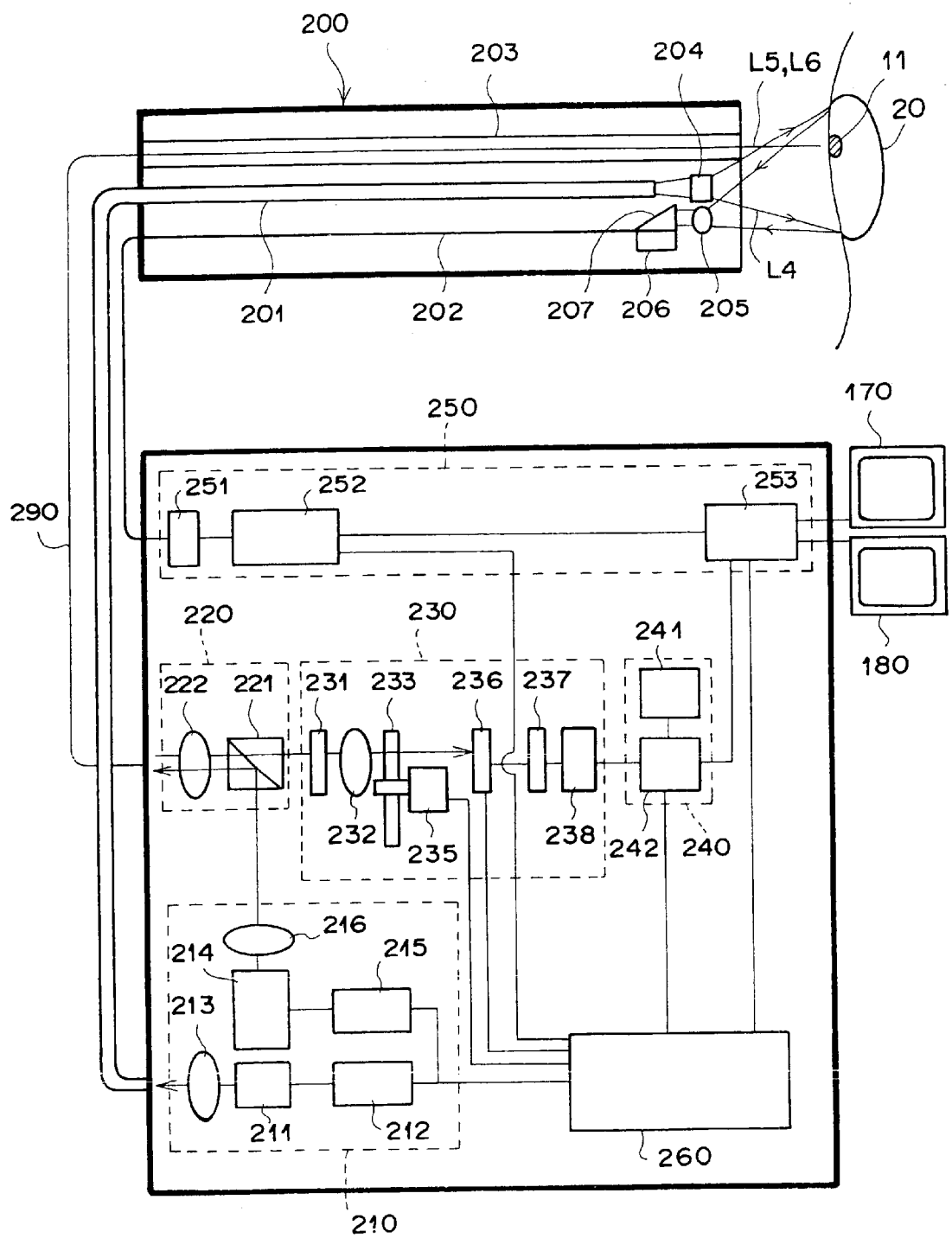
FIG. 3 is a schematic view showing an endoscope system, in which a second embodiment of the apparatus for displaying fluorescence information in accordance with the present invention is employed.

An endoscope system, in which a second embodiment of the apparatus for displaying fluorescence information in accordance with the present invention is employed, will be described hereinbelow with reference to FIG. 3 and FIG. 4. FIG. 3 is a schematic view showing the endoscope system, in which the second embodiment of the apparatus for displaying fluorescence information in accordance with the present invention is employed. In the endoscope system, in which the second embodiment of the apparatus for displaying fluorescence information in accordance with the present invention is employed, excitation light is irradiated to a measuring site in a living body, the excitation light causing the measuring site to produce fluorescence. The fluorescence produced from the measuring site is detected with a quartz fiber. In this manner, the fluorescence produced from a single point at the site in the living body is detected. Also, light intensity B' of fluorescence components of the fluorescence, which fluorescence components have wavelengths falling within a wavelength region of 480 nm±30 nm, and light intensity R' of fluorescence components of the fluorescence, which fluorescence components have wavelengths falling within a wavelength region of 630 nm±30 nm, are detected. Further, an R'-to-B' ratio is calculated, and information in accordance with the results of the calculation is displayed.

The endoscope system, in which the second embodiment of the apparatus for displaying fluorescence information in accordance with the present invention is employed, comprises an endoscope 200 to be inserted into a region of a patient, which region is considered as being a diseased part, and an illuminating unit 210 provided with light sources for producing white light, which is used when an ordinary image is to be displayed, and the excitation light, which is used when fluorescence information is to be displayed. The endoscope system also comprises optical path separating means 220 for separating an optical path of the excitation light and an optical path of measured fluorescence from each other. The endoscope system further comprises an R'-to-B' ratio calculating unit 230 for receiving the fluorescence, which is produced from the measuring site in the living body when the measuring site is exposed to the excitation light, and calculating the R'-to-B' ratio. The endoscope system still further comprises a comparison unit 240 for comparing a reference value, which has been stored previously, and the calculated R'-to-B' ratio with each other and feeding out a signal in accordance with the results of the comparison. The endoscope system also comprises an image processing unit 250 for performing image processing for displaying the ordinary image and the results of the comparison as visible images. The endoscope system further comprises a controller 260, which is connected to the respective units and controls operation timings. The endoscope system still further comprises the monitor 170 for displaying the ordinary image information, which has been obtained from the image processing performed by the image processing unit 250, as a visible image, and the monitor 180 for displaying the results of the comparison, which have been obtained from the image processing performed by the image processing unit 250. The endoscope system also comprises a quartz fiber 290 for guiding the excitation light and the fluorescence.

A light guide 201, a CCD cable 202, and a forceps hole 203 extend in the endoscope 200 up to a leading end of the endoscope 200. A quartz fiber 290 extends through the forceps hole 203. An illuminating lens 204 is located at a leading end of the light guide 201, i.e. at the leading end of the endoscope 200. An objective lens 205 is located at a leading end of the CCD cable 202, i.e. at the leading end of the endoscope 200. A CCD image sensor 206 is connected to the leading end of the CCD cable 202, and a mirror 207 is mounted on the CCD image sensor 206. A tail end of the light guide 201 is connected to the illuminating unit 210. A tail end of the CCD cable 202 is connected to the image processing unit 250. A tail end of the quartz fiber 290 is connected to the optical path separating means 220.

The illuminating unit 210 comprises a white light source 211 for producing white light L4, which is used when an ordinary image is to be displayed, and an electric power source 212, which is electrically connected to the white light source 211. The illuminating unit 210 also comprises a GaN type of semiconductor laser 214 for producing excitation light L5, which is used when fluorescence information is to be displayed, and an electric power source 215, which is electrically connected to the GaN type of semiconductor laser 214.

The optical path separating means 220 is provided with a dichroic mirror 221. The dichroic mirror 221 reflects the excitation light L5 coming from the GaN type of semiconductor laser 214 and causes the excitation light L5 to impinge upon the quartz fiber 290. Also, the dichroic mirror 221 transmits fluorescence L6, which has passed through the quartz fiber 290, toward the R'-to-B' ratio calculating unit 230.

The R'-to-B' ratio calculating unit 230 comprises an excitation light cut-off filter 231 for filtering out light, which has wavelengths in the vicinity of the wavelength of the excitation light L5, from the fluorescence L6 having passed through the quartz fiber 290. The R'-to-B' ratio calculating unit 230 also comprises a change-over filter 233 for extracting fluorescence components, which have wavelengths falling within a desired wavelength region, from the fluorescence L6 having passed through the excitation light cut-off filter 231. The R'-to-B' ratio calculating unit 230 further comprises a filter rotating device 235 for rotating the change-over filter 233. The R'-to-B' ratio calculating unit 230 still further comprises a photodetector 236 for measuring the light intensity of the fluorescence components having passed through the change-over filter 233. The R'-to-B' ratio calculating unit 230 also comprises a measured data memory 237 for storing measured data having been obtained from the photodetector 236, and R'-to-B' ratio calculating means 238 for calculating the R'-to-B' ratio from the values having been stored in the measured data memory 237.

Figure 4:
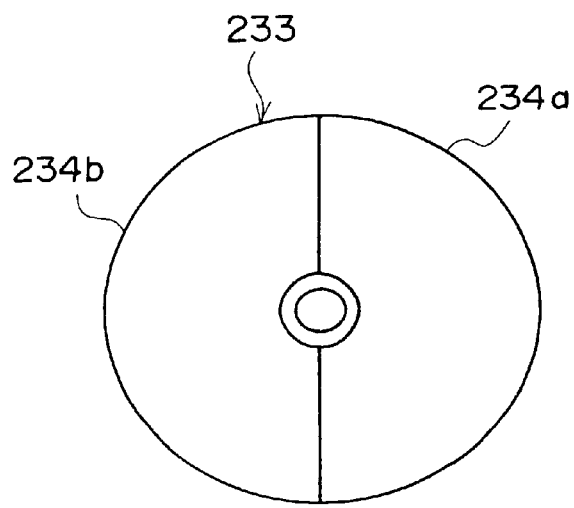
FIG. 4 is a schematic view showing a change-over filter, which is employed in the second embodiment.
Figure 5:
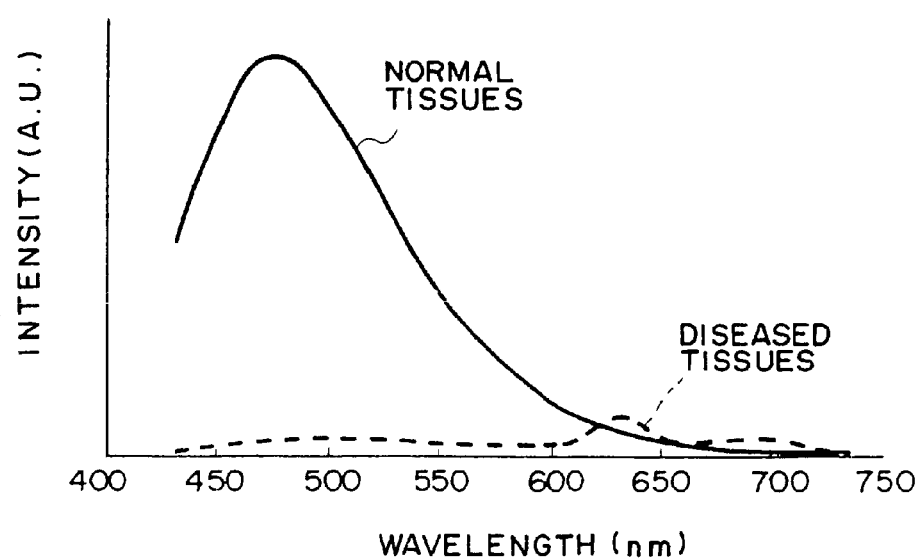
FIG. 5 is a graph showing spectral intensity distributions of fluorescence spectra of fluorescence produced from normal tissues and fluorescence produced from diseased tissues.

As illustrated in FIG. 4, the change-over filter 233 is constituted of an optical filter 234a and an optical filter 234b. The optical filter 234a is a band-pass filter, which transmits only light having wavelengths falling within a wavelength region of 480 nm±30 nm. The optical filter 234b is a band-pass filter, which transmits only light having wavelengths falling within a wavelength region of 630 nm±30 nm.

The comparison unit 240 comprises storage means 241 for storing a reference value RE'. The comparison unit 240 also comprises comparison means 242 for comparing the R'-to-B' ratio, which has been calculated by the R'-to-B' ratio calculating means 238, and the reference value RE', which has been stored in the storage means 241, with each other.

The reference value RE' is set in accordance with an R'-to-B' ratio having been calculated previously with respect to living body tissues, which have been found as being normal tissues or diseased tissues. The reference value RE' has been stored previously in the storage means 241.

The image processing unit 250 comprises an analog-to-digital converting circuit 251 for digitizing an image signal, which has been obtained from the CCD image sensor 206. The image processing unit 250 also comprises an ordinary image memory 252 for storing a digital ordinary image signal, which has been obtained from the analog-to-digital converting circuit 251. The image processing unit 250 further comprises a video signal processing circuit 253 for converting the image signal, which has been received from the ordinary image memory 252, and the results of the comparison, which have been obtained from the comparison means 242, into video signals.

How the endoscope system, in which the second embodiment of the apparatus for displaying fluorescence information in accordance with the present invention is employed, operates will be described hereinbelow. Firstly, how the endoscope system operates when an ordinary image is to be displayed will be described hereinbelow.

When an ordinary image is to be displayed, the electric power source 212 for the white light source 211 is driven in accordance with a control signal fed from the controller 260, and the white light L4 is produced by the white light source 211. The white light L4 passes through a lens 213 and impinges upon the light guide 201. The white light L4 is guided through the light guide 201 to the leading end of the endoscope 200, passes through the illuminating lens 204, and is irradiated to a region of interest 20 containing a measuring site 11.

The white light L4 reflected from the measuring site 11 is converged by the objective lens 205. The white light L4 is then reflected by the mirror 207, and the direction of the optical path of the white light L4 is changed by an angle of 90° by the mirror 207. An image of the reflected white light L4 is formed on the CCD image sensor 206. The image signal obtained from the CCD image sensor 206 is fed into the analog-to-digital converting circuit 251 and converted into the digital ordinary image signal. The digital ordinary image signal is stored in the ordinary image memory 252. The digital ordinary image signal is then fed from the ordinary image memory 252 into the video signal processing circuit 253 and converted into an analog ordinary image signal. The thus obtained analog ordinary image signal is fed into the monitor 170 and used for displaying a visible image on the monitor 170. The series of the operations described above are controlled by the controller 260.

How the endoscope system operates when fluorescence information is to be displayed will be described hereinbelow.

When fluorescence information is to be displayed, the electric power source 215 for the GaN type of semiconductor laser 214 is driven in accordance with a control signal fed from the controller 260, and the excitation light L5 having a wavelength of 410 nm is produced by the GaN type of semiconductor laser 214. The excitation light L5 passes through a lens 216 and impinges upon the dichroic mirror 221. The excitation light L5 is reflected from the dichroic mirror 221, passes through a lens 222, and impinges upon the quartz fiber 290. The excitation light L5 is guided through the quartz fiber 290, which passes through the forceps hole 203 of the endoscope 200. The excitation light L5 is thus guided to the vicinity of the measuring site 11 and is irradiated from the leading end of the quartz fiber 290 to the measuring site 11.

When the measuring site 11 is exposed to the excitation light L5, the fluorescence L6 is produced from the measuring site 11. The fluorescence L6 impinges upon the leading end of the quartz fiber 290, passes through the quartz fiber 290 and the lens 222, and travels toward the dichroic mirror 221. The dichroic mirror 221 has a structure such that it transmits light entering from the left side in FIG. 3. The fluorescence L6, which has passed through the dichroic mirror 221, passes through the excitation light cut-off filter 231 and a lens 232, and impinges upon the change-over filter 233. The excitation light cut-off filter 231 is a long-pass filter, which transmits the entire fluorescence having wavelengths of at least 420 nm and filters out light having wavelengths shorter than 420 nm. Since the wavelength of the excitation light L5 is 410 nm, the excitation light L5 having been reflected from the measuring site 11 is filtered out by the excitation light cut-off filter 231 and does not impinge upon the change-over filter 233.

In accordance with a control signal received from the controller 260, the filter rotating device 235 is driven, and the fluorescence L6 successively passes through the optical filter 234a or the optical filter 234b. The fluorescence L6, which has passed through the optical filter 234a or the optical filter 234b, impinges upon the photodetector 236, and the light intensity of the fluorescence L6 is detected by the photodetector 236. Also, in the measured data memory 237, in accordance with a control signal received from the controller 260, a signal representing the light intensity B' of the fluorescence components of the fluorescence L6, which fluorescence components have passed through the optical filter 234a of the change-over filter 233, is stored in a predetermined area of the measured data memory 237, and a signal representing the light intensity R' of the fluorescence components of the fluorescence L6, which fluorescence components have passed through the optical filter 234b of the change-over filter 233, is stored in a different area of the measured data memory 237.

The R'-to-B' ratio calculating means 238 calculates the R'-to-B' ratio from the signals representing the light intensity B' and the light intensity R' of the fluorescence L6 having been stored in the measured data memory 237.

The comparison means 242 compares the R'-to-B' ratio, which has been calculated by the R'-to-B' ratio calculating means 238, and the reference value RE', which has been stored in the storage means 241, with each other.

The results of the comparison are displayed on the monitor 180.

As described above, in the second embodiment, the fluorescence components of the fluorescence L6, which fluorescence components have wavelengths falling within the wavelength region of 480 nm±30 nm, and the fluorescence components of the fluorescence L6, which fluorescence components have wavelengths falling within the wavelength region of 630 nm±30 nm, are extracted from the fluorescence L6, which has been guided through the quartz fiber 290. Also, the light intensity B' of the fluorescence components, which have wavelengths falling within the wavelength region of 480 nm±30 nm, and the light intensity R' of the fluorescence components, which have wavelengths falling within the wavelength region of 630 nm±30 nm, are detected. Further, the R'-to-B' ratio is calculated and compared with the reference value RE', and the results of the comparison are displayed. Therefore, with the second embodiment, the information having enhanced reliability is capable of being displayed.

Also, with the second embodiment, the distance between the measuring site 11 and the leading end of the quartz fiber 290 is capable of being kept short. Therefore, even if the width of the detection wavelength region is set at a value of as short as 30 nm, a sufficient light intensity is capable of being obtained. In cases where the width of the extracted wavelength region is thus kept short, the information having reliability enhanced even further is capable of being displayed.

Further, with the second embodiment, wherein the GaN type of semiconductor laser 214, which produces the excitation light L5 having a wavelength of 410 nm, is employed as the excitation light irradiating means, the light intensity of the fluorescence is capable of being detected appropriately. Further, the size of the apparatus for displaying fluorescence information is capable of being kept small, and the cost of the apparatus is capable of being kept low.

Furthermore, with the second embodiment, the comparison is made as to whether the R'-to-B' ratio is at most equal to the reference value RE' or higher than the reference value RE', and the results of the comparison are displayed. Alternatively, the ratio obtained from the division of the light intensities of the two wavelength regions may be directly displayed. As another alternative, each of the light intensities may be displayed with an additive color process, and the ratio between the light intensities may be displayed as a change in tint on the display screen.

Also, in the first and second embodiments described above, the fluorescence components having wavelengths falling within the wavelength region in the vicinity of 480 nm and the fluorescence components having wavelengths falling within the wavelength region in the vicinity of 630 nm are extracted, and the ratio between the light intensities of the extracted fluorescence components is calculated. Alternatively, the fluorescence components having wavelengths falling within the wavelength region in the vicinity of 480 nm and the fluorescence components having wavelengths falling within the wavelength region in the vicinity of 700 nm may be extracted, and the ratio between the light intensities of the extracted fluorescence components may be calculated.

Figure 7:
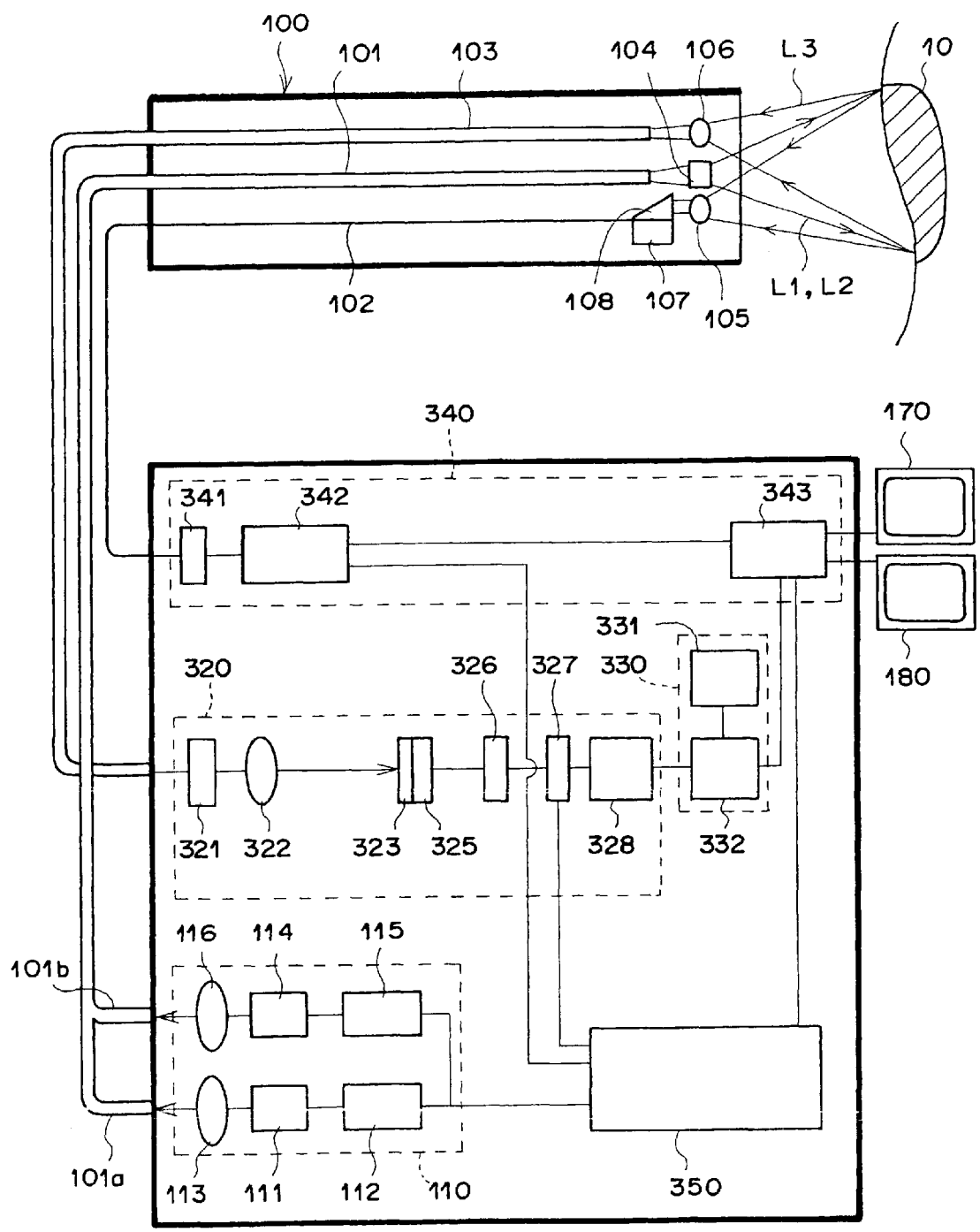
FIG. 7 is a schematic view showing an endoscope system, in which a third embodiment of the apparatus for displaying fluorescence information in accordance with the present invention is employed.

An endoscope system, in which a third embodiment of the apparatus for displaying fluorescence information in accordance with the present invention is employed, will be described hereinbelow with reference to FIG. 7 and FIG. 8. FIG. 7 is a schematic view showing the endoscope system, in which the third embodiment of the apparatus for displaying fluorescence information in accordance with the present invention is employed. In the endoscope system, in which the third embodiment of the apparatus for displaying fluorescence information in accordance with the present invention is employed, excitation light is irradiated to a measuring site in a living body, the excitation light causing the measuring site to produce fluorescence. The fluorescence produced from the measuring site is two-dimensionally detected with an image fiber and received by a high-sensitivity image sensor. Also, light intensity Ba' of fluorescence components of the fluorescence, which fluorescence components have wavelengths falling within a wavelength region of 480 nm±70 nm, and light intensity Wa of fluorescence components of the fluorescence, which fluorescence components have wavelengths falling within an entire measurement wavelength region, are detected. Further, a Ba'-to-Wa ratio is calculated, and information in accordance with the results of the calculation is displayed. In FIG. 7, similar elements are numbered with the same reference numerals with respect to FIG. 1.

The endoscope system, in which the third embodiment of the apparatus for displaying fluorescence information in accordance with the present invention is employed, comprises the endoscope 100 to be inserted into a region of a patient, which region is considered as being a diseased part, and the illuminating unit 110 provided with light sources for producing white light, which is used when an ordinary image is to be displayed, and the excitation light, which is used when fluorescence information is to be displayed. The endoscope system also comprises a Ba'-to-Wa ratio calculating unit 320 for receiving the fluorescence, which is produced from the measuring site in the living body when the measuring site is exposed to the excitation light, and calculating the Ba'-to-Wa ratio. The endoscope system further comprises a comparison unit 330 for comparing a reference value, which has been stored previously, and the calculated Ba'-to-Wa ratio with each other and feeding out a signal in accordance with the results of the comparison. The endoscope system still further comprises an image processing unit 340 for performing image processing for displaying the ordinary image and the results of the comparison as visible images. The endoscope system also comprises a controller 350, which is connected to the respective units and controls operation timings. The endoscope system further comprises a monitor 170 for displaying the ordinary image information, which has been obtained from the image processing performed by the image processing unit 340, as a visible image, and a monitor 180 for displaying the results of the comparison, which have been obtained from the image processing performed by the image processing unit 340.

The tail end of the image fiber 103 of the endoscope 100 is connected to the Ba'-to-Wa ratio calculating unit 320.

The Ba'-to-Wa ratio calculating unit 320 comprises an excitation light cut-off filter 321 for filtering out light, which has wavelengths falling within a wavelength region of at most 420 nm in the vicinity of the wavelength of the excitation light L2, from the fluorescence L3 having passed through the image fiber 103. The Ba'-to-Wa ratio calculating unit 320 also comprises a CCD image sensor 325 combined with a mosaic filter 323, which comprises two kinds of optical filters combined with each other in a mosaic-like form. The Ba'-to-Wa ratio calculating unit 320 further comprises an analog-to-digital converting circuit 326 for digitizing a fluorescence signal, which has been obtained from the CCD image sensor 325. The Ba'-to-Wa ratio calculating unit 320 still further comprises a fluorescence image memory 327 for storing a fluorescence image signal having been obtained from the analog-to-digital converting circuit 326. The Ba'-to-Wa ratio calculating unit 320 also comprises Ba'-to-Wa ratio calculating means 328 for calculating the Ba'-to-Wa ratio from the fluorescence image signal having been stored in the fluorescence image memory 327.

Figure 8:
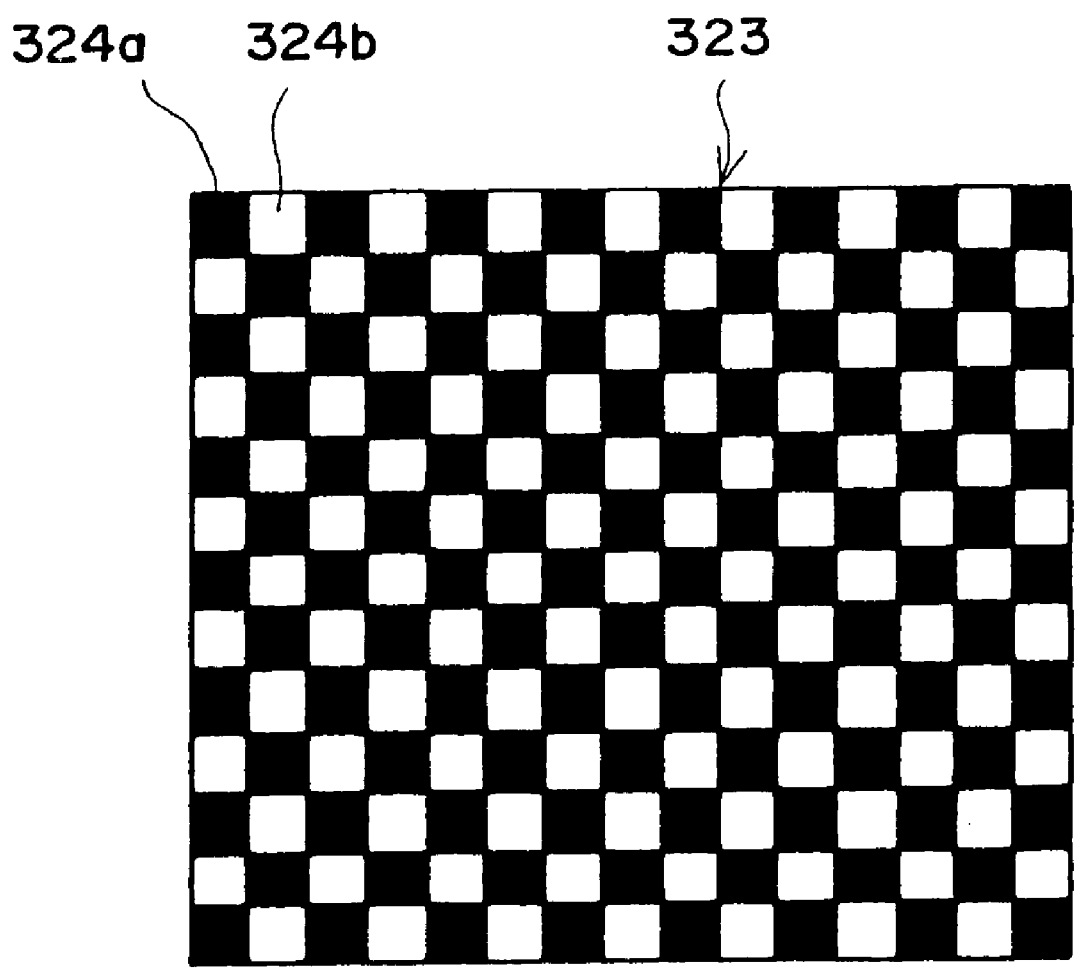
FIG. 8 is a schematic view showing a mosaic filter, which is employed in the third embodiment.

As illustrated in FIG. 8, the mosaic filter 323 is constituted of optical filters 324a, 324a, . . . and blank areas 324b, 324b, . . . The optical filters 324a, 324a, are band-pass filters, which transmit only light having wavelengths falling within a wavelength region of 480 nm±70 nm. The blank areas 324b, 324b, . . . transmit light having wavelengths falling within the entire measurement wavelength region.

The comparison unit 330 comprises storage means 331 for storing a reference value RE". The comparison unit 330 also comprises comparison means 332 for comparing the Ba'-to-Wa ratio, which has been calculated by the Ba'-to-Wa ratio calculating means 328, and the reference value RE", which has been stored in the storage means 331, with each other.

The reference value RE" is set in accordance with a Ba'-to-Wa ratio having been calculated previously with respect to living body tissues, which have been found as being normal tissues or diseased tissues.

The image processing unit 340 comprises an analog-to-digital converting circuit 341 for digitizing an image signal, which has been obtained from the CCD image sensor 107. The image processing unit 340 also comprises an ordinary image memory 342 for storing a digital ordinary image signal, which has been obtained from the analog-to-digital converting circuit 341. The image processing unit 340 further comprises a video signal processing circuit 343 for converting the image signal, which has been received from the ordinary image memory 342, and the results of the comparison, which have been obtained from the comparison means 332, into video signals.

How the endoscope system, in which the third embodiment of the apparatus for displaying fluorescence information in accordance with the present invention is employed, operates will be described hereinbelow. Firstly, how the endoscope system operates when an ordinary image is to be displayed will be described hereinbelow.

When an ordinary image is to be displayed, the electric power source 112 for the white light source 111 is driven in accordance with a control signal fed from the controller 350, and the white light L1 is produced by the white light source 111. The white light L1 passes through the lens 113 and impinges upon the white light guide 101a. The white light L1 is guided through the white light guide 101a to the leading end of the endoscope 100, passes through the illuminating lens 104, and is irradiated to a measuring site 10.

The white light L1 reflected from the measuring site 10 is converged by the objective lens 105 and reflected by the mirror 108, and an image of the reflected white light L1 is formed on the CCD image sensor 107. The image signal obtained from the CCD image sensor 107 is fed into the analog-to-digital converting circuit 341 and converted into the digital ordinary image signal. The digital ordinary image signal is stored in the ordinary image memory 342. The digital ordinary image signal is then fed from the ordinary image memory 342 into the video signal processing circuit 343 and converted into an analog ordinary image signal. The thus obtained analog ordinary image signal is fed into the monitor 170 and used for displaying a visible image on the monitor 170. The series of the operations described above are controlled by the controller 350.

How the endoscope system operates when fluorescence information is to be displayed will be described hereinbelow.

When fluorescence information is to be displayed, the electric power source 115 for the GaN type of semiconductor laser 114 is driven in accordance with a control signal fed from the controller 350, and the excitation light L2 having a wavelength of 410 nm is produced by the GaN type of semiconductor laser 114. The excitation light L2 passes through the lens 116 and impinges upon the excitation light guide 101b. The excitation light L2 is guided through the excitation light guide 101b to the leading end of the endoscope 100, passes through the illuminating lens 104, and is irradiated to the measuring site 10.

When the measuring site 10 is exposed to the excitation light L2, the fluorescence L3 is produced from the measuring site 10. The fluorescence L3 is converged by the converging lens 106 and impinges upon the leading end of the image fiber 103. The fluorescence L3 then passes through the image fiber 103 and impinges upon the excitation light cut-off filter 321.

Thereafter, the fluorescence L3 is converged by a lens 322 and passes through the mosaic filter 323, which is combined with the CCD image sensor 325. The fluorescence L3 is then received by the CCD image sensor 325, and a fluorescence image signal is obtained from the CCD image sensor 325. The fluorescence image signal having been obtained from the CCD image sensor 325 is fed into the analog-to-digital converting circuit 326 and converted into a digital fluorescence image signal. The digital fluorescence image signal having been obtained from the analog-to-digital converting circuit 326 is stored in the fluorescence image memory 327.

At this time, fluorescence image signal components representing fluorescence components of the fluorescence L3, which fluorescence components have passed through the optical filters 324a, 324a, . . . of the mosaic filter 323, and fluorescence image signal components representing fluorescence components of the fluorescence L3, which fluorescence components have passed through the blank areas 324b, 324b, . . . of the mosaic filter 323, are stored in different memory areas of the fluorescence image memory 327. Therefore, the fluorescence image signal components representing the fluorescence components, which have wavelengths falling within the wavelength region of 480 nm±70 nm, and the fluorescence image signal components representing the fluorescence components, which have wavelengths falling within the entire measurement wavelength region, are alternately stored in the memory areas of the fluorescence image memory 327.

The Ba'-to-Wa ratio calculating means 328 calculates the Ba'-to-Wa ratio with respect to each area of the measuring site 10 by utilizing the fluorescence image signal components, which have been stored in adjacent areas of the fluorescence image memory 327.

The comparison means 332 compares the Ba'-to-Wa ratio, which has been calculated by the Ba'-to-Wa ratio calculating means 328 and with respect to each area of the measuring site 10, and the reference value RE", which has been stored in the storage means 331, with each other.

The results of the comparison are displayed as an image on the monitor 180. In such cases, the display color with respect to the measured area is altered between when the Ba-to-Wa ratio is at most equal to the reference value RE' and when the Ba'-to-Wa ratio is higher than the reference value RE". Therefore, the measurer is capable of instantaneously recognize the results of the comparison.

Alternatively, instead of the comparison being made with respect to each pixel, the comparison processing may be made in units of pixels corresponding to binning processing of the CCD image sensor 325. As another alternative, the comparison may be made in units of an arbitrary pixel area, which is desired by the measurer. As a further alternative, the comparison may be made with respect to only an area specified by the measurer. As a still further alternative, pixels may be thinned out, and the comparison may then be made.

In cases where the comparison processing has not been made with respect to a certain area, the display color with respect to the certain area may be set at a predetermined color. In such cases, the area having been subjected to the comparison processing is capable of being displayed clearly. In cases where the pixels has been thinned out and then the comparison has been made, the results of the comparison corresponding to the pixels, which have been removed by the thinning-out process, may be interpolated from the results of the comparison corresponding to the neighboring pixels.

As described above, in the third embodiment, the fluorescence components of the fluorescence L3, which fluorescence components have wavelengths falling within the wavelength region of 480 nm±70 nm, and the fluorescence components of the fluorescence L3, which fluorescence components have wavelengths falling within the entire measurement wavelength region, are extracted from the fluorescence L3, which is produced from the measuring site 10 when the excitation light L2 is irradiated to the measuring site 10. Also, the light intensity Ba' of the fluorescence components, which have wavelengths falling within the wavelength region of 480 nm±70 nm, and the light intensity Wa of the fluorescence components, which have wavelengths falling within the entire measurement wavelength region, are detected. Further, the Ba'-to-Wa ratio is calculated and compared with the reference value RE", and the results of the comparison are displayed. Therefore, with the third embodiment, the information having enhanced reliability is capable of being displayed. Furthermore, since the Ba'-to-Wa ratio between the light intensities is compared with the reference value RE", adverse effects of fluctuations in spectral intensity due to fluctuations in measurement conditions, such as the measurement distance and the measurement angle, are capable of being reduced, and the information having reliability enhanced even further is capable of being displayed.

Also, with the third embodiment, wherein the fluorescence L3 is detected two-dimensionally with the CCD image sensor 325, the information concerning the fluorescence over a wide range is capable of being displayed quickly.

Further, with the third embodiment, wherein the GaN type of semiconductor laser 114, which produces the excitation light L2 having a wavelength of 410 nm, is employed as the excitation light irradiating means, the light intensity of the fluorescence is capable of being detected appropriately. Further, the size of the apparatus for displaying fluorescence information is capable of being kept small, and the cost of the apparatus is capable of being kept low.

As illustrated in FIG. 8, in the third embodiment, the mosaic filter 323 is constituted of the optical filters 324a, 324a, . . . , which transmits only light having wavelengths falling within the wavelength region of 480 nm±70 nm, and the blank areas 324b, 324b, . . . , which transmits light having wavelengths falling within the entire measurement wavelength region. Alternatively, a mosaic filter, which is constituted of the optical filters 324a, 324a, . . . , the blank areas 324b, 324b, . . . , and optical filters necessary for obtaining an ordinary image, may be located in front of the CCD image sensor 325. In such cases, the CCD image sensor 325 is capable of being utilized for both the detection of the ordinary image and the detection of the fluorescence.

Furthermore, a CCD image sensor combined with the aforesaid mosaic filter, which is constituted of the optical filters 324a, 324a, . . . , the blank areas 324b, 324b, . . . , and the optical filters necessary for obtaining an ordinary image, may be located at the leading end of the endoscope 100. In such cases, the CCD image sensor is capable of being utilized for both the detection of the ordinary image and the detection of the fluorescence.

Also, in the third embodiment, the comparison is made as to whether the Ba'-to-Wa ratio is at most equal to the reference value RE" or higher than the reference value RE", and the results of the comparison are displayed. Alternatively, the light intensities of the two wavelength regions may be displayed with the additive color process, and the ratio between the light intensities may be displayed as a change in tint on the display screen. As another alternative, the light intensities of the two wavelength regions may be divided by each other, and the value obtained from the division may be displayed as a change in luminance or tint.

Figure 9:
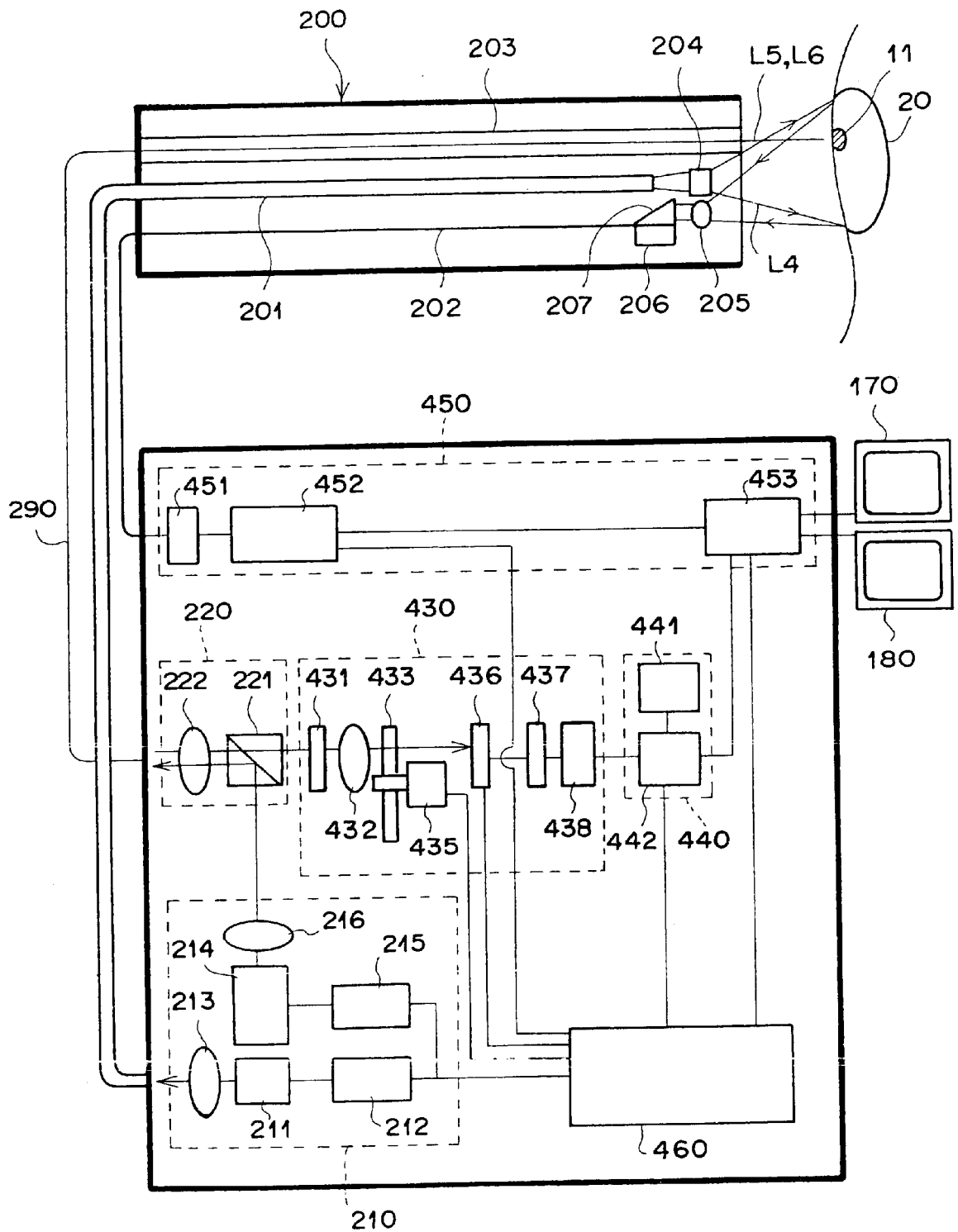
FIG. 9 is a schematic view showing an endoscope system, in which a fourth embodiment of the apparatus for displaying fluorescence information in accordance with the present invention is employed.

An endoscope system, in which a fourth embodiment of the apparatus for displaying fluorescence information in accordance with the present invention is employed, will be described hereinbelow with reference to FIG. 9 and FIG. 10. FIG. 9 is a schematic view showing the endoscope system, in which the fourth embodiment of the apparatus for displaying fluorescence information in accordance with the present invention is employed. In the endoscope system, in which the fourth embodiment of the apparatus for displaying fluorescence information in accordance with the present invention is employed, excitation light is irradiated to a measuring site in a living body, the excitation light causing the measuring site to produce fluorescence. The fluorescence produced from the measuring site is detected with a quartz fiber. In this manner, the fluorescence produced from a single point at the site in the living body is detected. Also, light intensity Bb' of fluorescence components of the fluorescence, which fluorescence components have wavelengths falling within a wavelength region of 480 nm±30 nm, and light intensity Wb of fluorescence components of the fluorescence, which fluorescence components have wavelengths falling within the entire measurement wavelength region, are detected. Further, a Bb'-to-Wb ratio is calculated, and information in accordance with the results of the calculation is displayed. In FIG. 9, similar elements are numbered with the same reference numerals with respect to FIG. 3.

The endoscope system, in which the fourth embodiment of the apparatus for displaying fluorescence information in accordance with the present invention is employed, comprises the endoscope 200 to be inserted into a region of a patient, which region is considered as being a diseased part, and the illuminating unit 210 provided with light sources for producing white light, which is used when an ordinary image is to be displayed, and the excitation light, which is used when fluorescence information is to be displayed. The endoscope system also comprises the optical path separating means 220 for separating an optical path of the excitation light and an optical path of measured fluorescence from each other. The endoscope system further comprises a Bb'-to-Wb ratio calculating unit 430 for receiving the fluorescence, which is produced from the measuring site in the living body when the measuring site is exposed to the excitation light, and calculating the Bb'-to-Wb ratio. The endoscope system still further comprises a comparison unit 440 for comparing a reference value, which has been stored previously, and the calculated Bb'-to-Wb ratio with each other and feeding out a signal in accordance with the results of the comparison. The endoscope system also comprises an image processing unit 450 for performing image processing for displaying the ordinary image and the results of the comparison as visible images. The endoscope system further comprises a controller 460, which is connected to the respective units and controls operation timings. The endoscope system still further comprises the monitor 170 for displaying the ordinary image information, which has been obtained from the image processing performed by the image processing unit 450, as a visible image, and the monitor 180 for displaying the results of the comparison, which have been obtained from the image processing performed by the image processing unit 450. The endoscope system also comprises the quartz fiber 290 for guiding the excitation light and the fluorescence.

The tail end of the CCD cable 202 of the endoscope 200 is connected to the image processing unit 450.

The optical path separating means 220 is provided with the dichroic mirror 221. The dichroic mirror 221 reflects the excitation light L5 coming from the GaN type of semiconductor laser 214 and causes the excitation light L5 to impinge upon the quartz fiber 290. Also, the dichroic mirror 221 transmits the fluorescence L6, which has passed through the quartz fiber 290, toward the Bb'-to-Wb ratio calculating unit 430.

The Bb'-to-Wb ratio calculating unit 430 comprises an excitation light cut-off filter 431 for filtering out light, which has wavelengths in the vicinity of the wavelength of the excitation light L5, from the fluorescence L6 having passed through the quartz fiber 290. The Bb'-to-Wb ratio calculating unit 430 also comprises a change-over filter 433 for extracting fluorescence components, which have wavelengths falling within a desired wavelength region, from the fluorescence L6 having passed through the excitation light cut-off filter 431. The Bb'-to-Wb ratio calculating unit 430 further comprises a filter rotating device 435 for rotating the change-over filter 433. The Bb'-to-Wb ratio calculating unit 430 still further comprises a photodetector 436 for measuring the light intensity of the fluorescence components having passed through the change-over filter 433. The Bb'-to-Wb ratio calculating unit 430 also comprises a measured data memory 437 for storing measured data having been obtained from the photodetector 436, and Bb'-to-Wb ratio calculating means 438 for calculating the Bb'-to-Wb ratio from the values having been stored in the measured data memory 437.

Figure 10:
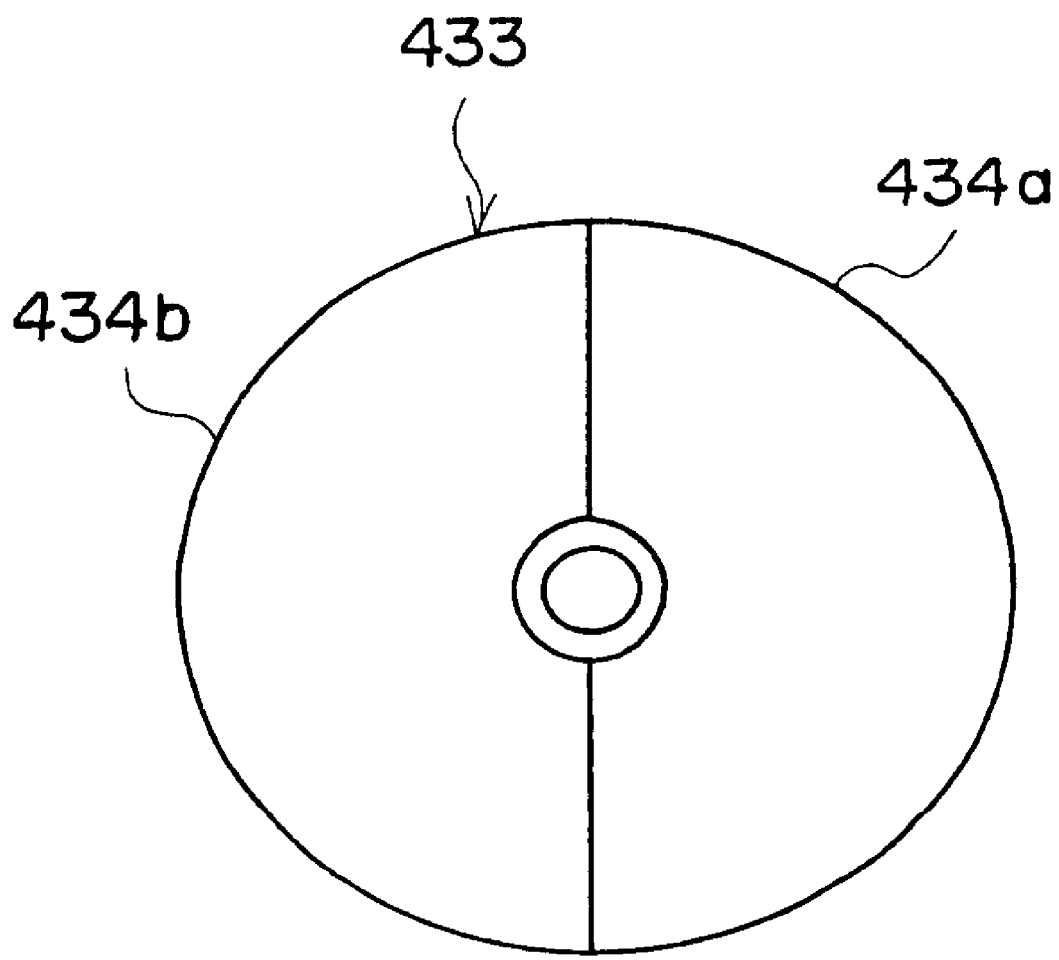
FIG. 10 is a schematic view showing a change-over filter, which is employed in the fourth embodiment.
Figure 12:
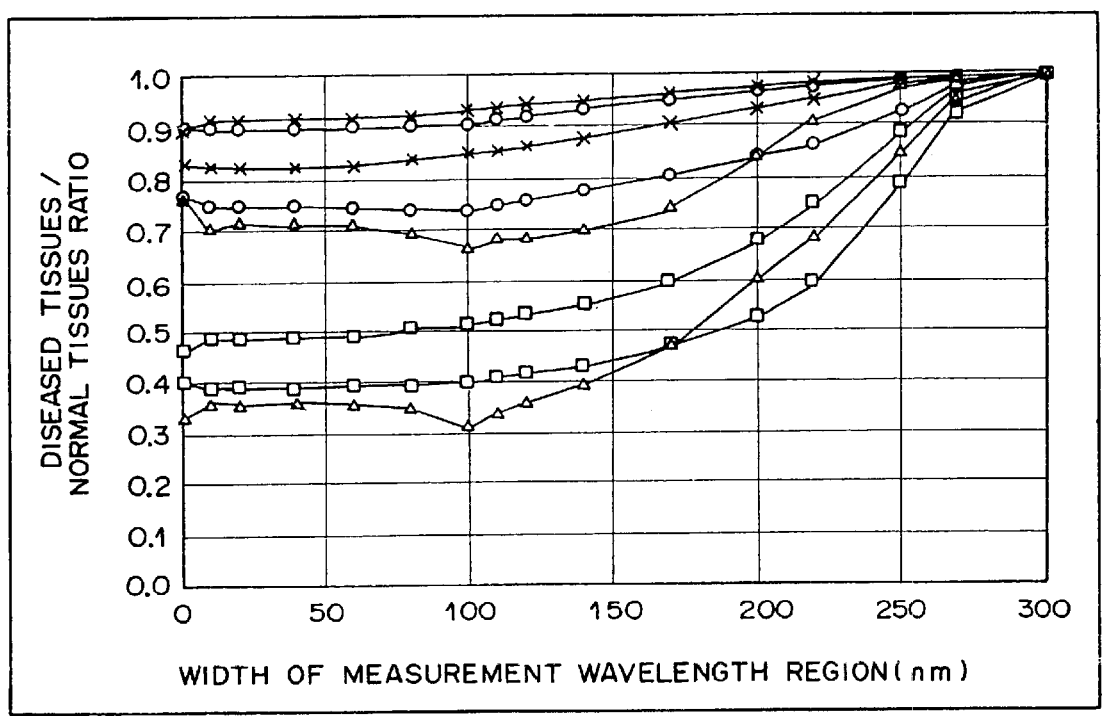
FIG. 12 is a graph showing relationship between a width of a measurement wavelength region and a ratio of a light intensity ratio, which has been calculated from fluorescence produced from diseased tissues and with respect to a set measurement wavelength region width and an entire measurement wavelength region, to a light intensity ratio, which has been calculated from fluorescence produced from normal tissues and with respect to the set measurement wavelength region width and the entire measurement wavelength region.

As illustrated in FIG. 10, the change-over filter 433 is constituted of an optical filter 434a and a blank area 434b. The optical filter 434a is a band-pass filter, which transmits only light having wavelengths falling within a wavelength region of 480 nm±30 nm. The blank area 434b transmits light having wavelengths falling within the entire measurement wavelength region.

The comparison unit 440 comprises storage means 441 for storing a reference value RE'''. The comparison unit 440 also comprises comparison means 442 for comparing the Bb'-to-Wb ratio, which has been calculated by the Bb' -to-Wb ratio calculating means 438, and the reference value RE''', which has been stored in the storage means 441, with each other.

The reference value RE''' is set in accordance with a Bb'-to-Wb ratio having been calculated previously with respect to living body tissues, which have been found as being normal tissues or diseased tissues. The reference value RE''' has been stored previously in the storage means 441.

The image processing unit 450 comprises an analog-to-digital converting circuit 451 for digitizing an image signal, which has been obtained from the CCD image sensor 206. The image processing unit 450 also comprises an ordinary image memory 452 for storing a digital ordinary image signal, which has been obtained from the analog-to-digital converting circuit 451. The image processing unit 450 further comprises a video signal processing circuit 453 for converting the image signal, which has been received from the ordinary image memory 452, and the results of the comparison, which have been obtained from the comparison means 442, into video signals.

How the endoscope system, in which the fourth embodiment of the apparatus for displaying fluorescence information in accordance with the present invention is employed, operates will be described hereinbelow. Firstly, how the endoscope system operates when an ordinary image is to be displayed will be described hereinbelow.

When an ordinary image is to be displayed, the electric power source 212 for the white light source 211 is driven in accordance with a control signal fed from the controller 460, and the white light L4 is produced by the white light source 211. The white light L4 passes through the lens 213 and impinges upon the light guide 201. The white light L4 is guided through the light guide 201 to the leading end of the endoscope 200, passes through the illuminating lens 204, and is irradiated to the region of interest 20 containing the measuring site 11.

The white light L4 reflected from the measuring site 11 is converged by the objective lens 205. The white light L4 is then reflected by the mirror 207, and the direction of the optical path of the white light L4 is changed by an angle of 90° by the mirror 207. An image of the reflected white light L4 is formed on the CCD image sensor 206. The image signal obtained from the CCD image sensor 206 is fed into the analog-to-digital converting circuit 451 and converted into the digital ordinary image signal. The digital ordinary image signal is stored in the ordinary image memory 452. The digital ordinary image signal is then fed from the ordinary image memory 452 into the video signal processing circuit 453 and converted into an analog ordinary image signal. The thus obtained analog ordinary image signal is fed into the monitor 170 and used for displaying a visible image on the monitor 170. The series of the operations described above are controlled by the controller 460.

How the endoscope system operates when fluorescence information is to be displayed will be described hereinbelow.

When fluorescence information is to be displayed, the electric power source 215 for the GaN type of semiconductor laser 214 is driven in accordance with a control signal fed from the controller 460, and the excitation light L5 having a wavelength of 410 nm is produced by the GaN type of semiconductor laser 214. The excitation light L5 passes through the lens 216 and impinges upon the dichroic mirror 221. The excitation light L5 is reflected from the dichroic mirror 221, passes through the lens 222, and impinges upon the quartz fiber 290. The excitation light L5 is guided through the quartz fiber 290, which passes through the forceps hole 203 of the endoscope 200. The excitation light L5 is thus guided to the vicinity of the measuring site 11 and is irradiated from the leading end of the quartz fiber 290 to the measuring site 11.

When the measuring site 11 is exposed to the excitation light L5, the fluorescence L6 is produced from the measuring site 11. The fluorescence L6 impinges upon the leading end of the quartz fiber 290, passes through the quartz fiber 290 and the lens 222, and travels toward the dichroic mirror 221. The dichroic mirror 221 has a structure such that it transmits light entering from the left side in FIG. 9. The fluorescence L6, which has passed through the dichroic mirror 221, passes through the excitation light cut-off filter 431 and a lens 432, and impinges upon the change-over filter 433. The excitation light cut-off filter 431 is a long-pass filter, which transmits the entire fluorescence having wavelengths of at least 420 nm and filters out light having wavelengths shorter than 420 nm. Since the wavelength of the excitation light L5 is 410 nm, the excitation light L5 having been reflected from the measuring site 11 is filtered out by the excitation light cut-off filter 431 and does not impinge upon the change-over filter 433.

In accordance with a control signal received from the controller 460, the filter rotating device 435 is driven, and the fluorescence L6 successively passes through the optical filter 434a or the blank area 434b. The fluorescence L6, which has passed through the optical filter 434a or the blank area 434b, impinges upon the photodetector 436, and the light intensity of the fluorescence L6 is detected by the photodetector 436. Also, in the measured data memory 437, in accordance with a control signal received from the controller 460, a signal representing the light intensity Bb' of the fluorescence components of the fluorescence L6, which fluorescence components have passed through the optical filter 434a of the change-over filter 433, is stored in a predetermined area of the measured data memory 437, and a signal representing the light intensity Wb of the fluorescence components of the fluorescence L6, which fluorescence components have passed through the blank area 434b of the change-over filter 433, is stored in a different area of the measured data memory 437.

The Bb'-to-Wb ratio calculating means 438 calculates the Bb' -to-Wb ratio from the signals representing the light intensity Bb' and the light intensity Wb of the fluorescence L6 having been stored in the measured data memory 437.

The comparison means 442 compares the Bb'-to-Wb ratio, which has been calculated by the Bb'-to-Wb ratio calculating means 438, and the reference value RE''', which has been stored in the storage means 441, with each other.

The results of the comparison are displayed on the monitor 180.

As described above, in the fourth embodiment, the fluorescence components of the fluorescence L6, which fluorescence components have wavelengths falling within the wavelength region of 480 nm±30 nm, and the fluorescence components of the fluorescence L6, which fluorescence components have wavelengths falling within the entire measurement wavelength region, are extracted from the fluorescence L6, which has been guided through the quartz fiber 290. Also, the light intensity Bb' of the fluorescence components, which have wavelengths falling within the wavelength region of 480 nm±30 nm, and the light intensity Wb of the fluorescence components, which have wavelengths falling within the entire measurement wavelength region, are detected. Further, the Bb'-to-Wb ratio is calculated and compared with the reference value RE''', and the results of the comparison are displayed. Therefore, with the fourth embodiment, the information having enhanced reliability is capable of being displayed. Furthermore, since the Bb'-to-Wb ratio between the light intensities is compared with the reference value RE''', adverse effects of fluctuations in spectral intensity due to fluctuations in measurement conditions, such as the measurement distance and the measurement angle, are capable of being reduced, and the information having reliability enhanced even further is capable of being displayed.

Also, with the fourth embodiment, the distance between the measuring site 11 and the leading end of the quartz fiber 290 is capable of being kept short. Therefore, even if the width of the detection wavelength region is set at a value of as short as 30 nm, a sufficient light intensity is capable of being obtained. In cases where the width of the extracted wavelength region is thus kept short, the information having reliability enhanced even further is capable of being displayed.

Further, with the fourth embodiment, wherein the GaN type of semiconductor laser 214, which produces the excitation light L5 having a wavelength of 410 nm, is employed as the excitation light irradiating means, the light intensity of the fluorescence is capable of being detected appropriately. Further, the size of the apparatus for displaying fluorescence information is capable of being kept small, and the cost of the apparatus is capable of being kept low.

Furthermore, in the fourth embodiment, the comparison is made as to whether the Bb'-to-Wb ratio is at most equal to the reference value RE''' or higher than the reference value RE''', and the results of the comparison are displayed. Alternatively, the light intensities of the two wavelength regions may be displayed with the additive color process, and the ratio between the light intensities may be displayed as a change in tint on the display screen. As another alternative, the light intensities of the two wavelength regions may be divided by each other, and the value obtained from the division may be displayed as a change in luminance or tint.

Also, in the third and fourth embodiments described above, the fluorescence components having wavelengths falling within the wavelength region in the vicinity of 480 nm and the fluorescence components having wavelengths falling within the entire measurement wavelength region are extracted, and the ratio between the light intensities of the extracted fluorescence components is calculated. Alternatively, in lieu of the fluorescence components having wavelengths falling within the wavelength region in the vicinity of 480 nm, the fluorescence components having wavelengths falling within the wavelength region in the vicinity of 630 nm or the fluorescence components having wavelengths falling within the wavelength region in the vicinity of 700 nm may be extracted. Also, the ratio between the light intensity of the thus extracted fluorescence components and the light intensity Wb of the fluorescence components having wavelengths falling within the entire measurement wavelength region may be calculated.

Further, in the third and fourth embodiments described above, the information in accordance with the ratio between the light intensity of the wavelength region in the vicinity of 480 nm and the light intensity of the entire measurement wavelength region is displayed. Alternatively, information in accordance with only the light intensity of the wavelength region in the vicinity of 480 nm may be displayed. For example, the light intensity of the wavelength region in the vicinity of 480 nm may be detected from the fluorescence produced from each of the normal tissues and the diseased tissues, and reference values may be stored previously. Also, the light intensity B of the wavelength region in the vicinity of 480 nm may be detected from the fluorescence produced from the measuring site and may be compared with the reference values. Further, the results of the comparison may be displayed. In cases where only the light intensity B of the wavelength region in the vicinity of 480 nm is detected, it is sufficient for the used filter to be constituted of only the optical filter, which transmits light having wavelengths falling within the wavelength region in the vicinity of 480 nm, and therefore the optical system is capable of being simplified.

Furthermore, the third and fourth embodiments may be modified such that information in accordance with both the light intensity of the wavelength region in the vicinity of 480 nm and the ratio between the light intensity of the entire measurement wavelength region and the light intensity of the wavelength region in the vicinity of 480 nm, 630 nm, or 700 nm is displayed. For example, a reference value corresponding to the light intensity of the wavelength region in the vicinity of 480 nm and a reference value corresponding to the ratio between the light intensity of the entire measurement wavelength region and the light intensity of the wavelength region in the vicinity of 480 nm, 630 nm, or 700 nm may be stored previously. Also, only in cases where both the light intensity of the wavelength region in the vicinity of 480 nm and the light intensity ratio described above take values close to the reference values for the normal tissues, the results of the comparison may be displayed as approximately representing that the tissues at the measuring site are the normal tissues. In such cases, there is little possibility that the fluorescence produced from the diseased tissues will be displayed by mistake as being close to the fluorescence produced from the normal tissues. Therefore, the technique described above is advantageous in cases where, for example, the measuring site has a strong probability of being the diseased tissues as in cases where the fluorescence detection is performed with respect to a living body having a previous illness.

As a different example, in cases where either one of the light intensity and the light intensity ratio takes a value approximately indicating the normal tissues when the value is compared with the reference value, the results of the comparison may be displayed as approximately representing that the tissues at the measuring site are the normal tissues. In such cases, there is little possibility that the fluorescence produced from the normal tissues will be displayed by mistake as being close to the fluorescence produced from the diseased tissues. Therefore, the technique described above is advantageous in cases where, for example, the measuring site has little probability of being the diseased tissues.

In cases where the information in accordance with both the light intensity and the light intensity ratio is displayed in the manner described above, the kinds of the optical filters, which constitute the mosaic filter or the change-over filter, may be increased, and the fluorescence components having wavelengths falling within desired wavelength regions may thereby be extracted. Also, in cases where the information in accordance with both the light intensity B of the wavelength region in the vicinity of 480 nm and the ratio between the light intensity of the entire measurement wavelength region and the light intensity of the wavelength region in the vicinity of 480 nm is displayed, the optical filter, which transmits light having wavelengths falling within the wavelength region in the vicinity of 480 nm, may be utilized for both the detection of the light intensity B and the detection of the light intensity ratio.

In the first, second, third, and fourth embodiments described above, the monitor 170 for displaying the ordinary image and the monitor 180 for displaying the results of the comparison are provided as two independent monitors. Alternatively, a single monitor may act as both the monitor 170 and the monitor 180. In such cases, display modes may be automatically changed over in a time series change-over manner. Alternatively, the display modes may be changed over by the measurer with change-over means.

Also, in the first, second, third, and fourth embodiments described above, the GaN type of semiconductor laser and the white light source are provided as two independent devices. Alternatively, by the utilization of an appropriate optical transmission filter, a single light source may act as both the excitation light source and the white light source.

Further, the first, second, third, and fourth embodiments described above may be modified in various ways. For example, the excitation light guiding fiber and the fluorescence guiding fiber may be separated from each other. Also, the ordinary image may be acquired with an image fiber.

In addition, all of the contents of Japanese Patent Application Nos. 11(1999)-312942 and 11(1999)312943 are incorporated into this specification by reference.

What is claimed is:

1. A method of displaying fluorescence information, comprising the steps of:
   i) irradiating excitation light to a measuring site in a living body, the excitation light causing the measuring site to produce fluorescence,
   ii) detecting light intensity of fluorescence components of the fluorescence produced by the measuring site, which fluorescence components have wavelengths falling within a predetermined wavelength region containing 480 nm,
   iii) detecting light intensity of fluorescence components of the fluorescence produced by the measuring site, which fluorescence components have wavelengths falling within a predetermined wavelength region containing either one of 630 nm and 700 nm, and
   iv) displaying information in accordance with a ratio between the two detected light intensities.

2. An apparatus for displaying fluorescence information, comprising:
   i) excitation light irradiating means for irradiating excitation light to a measuring site in a living body, the excitation light causing the measuring site to produce fluorescence,
   ii) first fluorescence intensity detecting means for detecting light intensity of fluorescence components of the fluorescence produced by the measuring site, which fluorescence components have wavelengths falling within a predetermined wavelength region containing 480 nm,
   iii) second fluorescence intensity detecting means for detecting light intensity of fluorescence components of the fluorescence produced by the measuring site, which fluorescence components have wavelengths falling within a predetermined wavelength region containing either one of 630 nm and 700 nm, and
   iv) displaying means for displaying information in accordance with a ratio between the light intensity, which has been detected by the first fluorescence intensity detecting means, and the light intensity, which has been detected by the second fluorescence intensity detecting means.

3. An apparatus as defined in claim 2 wherein the first fluorescence intensity detecting means comprises:
   first wavelength selecting means for selecting the fluorescence components of the fluorescence produced by the measuring site, which fluorescence components have wavelengths falling within the predetermined wavelength region containing 480 nm, and
   first light intensity detecting means for detecting the light intensity of the fluorescence components having been selected by the first wavelength selecting means, and
   the second fluorescence intensity detecting means comprises:
   second wavelength selecting means for selecting the fluorescence components of the fluorescence produced by the measuring site, which fluorescence components have wavelengths falling within the predetermined wavelength region containing either one of 630 nm and 700 nm, and
   second light intensity detecting means for detecting the light intensity of the fluorescence components having been selected by the second wavelength selecting means.

4. An apparatus as defined in claim 3 wherein the first wavelength selecting means selects the fluorescence components of the fluorescence produced by the measuring site, which fluorescence components have wavelengths falling within the predetermined wavelength region of 480 nm ±at most 70 nm, and the second wavelength selecting means selects the fluorescence components of the fluorescence produced by the measuring site, which fluorescence components have wavelengths falling within the predetermined wavelength region of either one of 630 nm±at most 70 nm and 700 nm at most 70 nm.

5. An apparatus as defined in claim 2, 3, or 4 wherein the excitation light has wavelengths falling within the range of 380 nm to 420 nm.

6. An apparatus as defined in claim 2, 3, or 4 wherein the excitation light irradiating means is a GaN type of semiconductor laser.

7. A method of displaying fluorescence information, comprising the steps of:
   i) irradiating excitation light to a measuring site in a living body, the excitation light causing the measuring site to produce fluorescence,
   ii) detecting light intensity W of fluorescence components of the fluorescence produced by the measuring site, which fluorescence components have wavelengths falling within an entire measurement wavelength region,
   iii) detecting at least one light intensity selected from among:
      light intensity B' of fluorescence components of the fluorescence produced by the measuring site, which fluorescence components have wavelengths falling within a wavelength region of 480 nm±at most 70 nm and at least containing 450 nm to 480 nm,
      light intensity R1 of fluorescence components of the fluorescence produced by the measuring site, which fluorescence components have wavelengths falling within a wavelength region of 630 nm±at most 70 nm and at least containing 600 nm to 630 nm, and
      light intensity R2 of fluorescence components of the fluorescence produced by the measuring site, which fluorescence components have wavelengths falling within a wavelength region of 700 nm±at most 70 nm and at least containing 700 nm to 710 nm, and
   iv) displaying information in accordance with a ratio between the at least one selected light intensity and the light intensity W.

8. A method of displaying fluorescence information, comprising the steps of:
   i) irradiating excitation light to a measuring site in a living body, the excitation light causing the measuring site to produce fluorescence,
   ii) detecting light intensity B of fluorescence components of the fluorescence produced by the measuring site, which fluorescence components have wavelengths falling within a wavelength region of 480 nm±at most 70 nm and at least containing 450 nm to 480 nm,
   iii) detecting light intensity W of fluorescence components of the fluorescence produced by the measuring site, which fluorescence components have wavelengths falling within an entire measurement wavelength region,
   iv) detecting at least one light intensity selected from among:
      light intensity B' of fluorescence components of the fluorescence produced by the measuring site, which fluorescence components have wavelengths falling within a wavelength region of 480 nm±at most 70 nm and at least containing 450 nm to 480 nm,
      light intensity R1 of fluorescence components of the fluorescence produced by the measuring site, which fluorescence components have wavelengths falling within a wavelength region of 630 nm±at most 70 nm and at least containing 600 nm to 630 nm, and
      light intensity R2 of fluorescence components of the fluorescence produced by the measuring site, which fluorescence components have wavelengths falling within a wavelength region of 700 nm±at most 70 nm and at least containing 700 nm to 710 nm, and
   v) displaying information in accordance with the light intensity B and a ratio between the at least one light intensity, which is selected from among the light intensities B', R1, and R2, and the light intensity W.

9. An apparatus for displaying fluorescence information, comprising:
   i) excitation light irradiating means for irradiating excitation light to a measuring site in a living body, the excitation light causing the measuring site to produce fluorescence,
   ii) second light intensity detecting means for detecting light intensity W of fluorescence components of the fluorescence produced by the measuring site, which fluorescence components have wavelengths falling within an entire measurement wavelength region,
   iii) at least one light intensity detecting means selected from among:
      third light intensity detecting means for detecting light intensity B' of fluorescence components of the fluorescence produced by the measuring site, which fluorescence components have wavelengths falling within a wavelength region of 480 nm±at most 70 nm and at least containing 450 nm to 480 nm,
      fourth light intensity detecting means for detecting light intensity R1 of fluorescence components of the fluorescence produced by the measuring site, which fluorescence components have wavelengths falling within a wavelength region of 630 nm±at most 70 nm and at least containing 600 nm to 630 nm, and
      fifth light intensity detecting means for detecting light intensity R2 of fluorescence components of the fluorescence produced by the measuring site, which fluorescence components have wavelengths falling within a wavelength region of 700 nm±at most 70 nm and at least containing 700 nm to 710 nm, and
   iv) fluorescence information displaying means for displaying information in accordance with a ratio between the light intensity, which has been detected by the at least one selected light intensity detecting means, and the light intensity W.

10. An apparatus for displaying fluorescence information, comprising:
    i) excitation light irradiating means for irradiating excitation light to a measuring site in a living body, the excitation light causing the measuring site to produce fluorescence,
    ii) first light intensity detecting means for detecting light intensity B of fluorescence components of the fluorescence produced by the measuring site, which fluorescence components have wavelengths falling within a wavelength region of 480 nm±at most 70 nm and at least containing 450 nm to 480 nm,
    iii) second light intensity detecting means for detecting light intensity W of fluorescence components of the fluorescence produced by the measuring site, which fluorescence components have wavelengths falling within an entire measurement wavelength region, iv) at least one light intensity detecting means selected from among:
   third light intensity detecting means for detecting light intensity B' of fluorescence components of the fluorescence produced by the measuring site, which fluorescence components have wavelengths falling within a wavelength region of 480 nm±at most 70 nm and at least containing 450 nm to 480 nm,
   fourth light intensity detecting means for detecting light intensity R1 of fluorescence components of the fluorescence produced by the measuring site, which fluorescence components have wavelengths falling within a wavelength region of 630 nm±at most 70 nm and at least containing 600 nm to 630 nm, and
   fifth light intensity detecting means for detecting light intensity R2 of fluorescence components of the fluorescence produced by the measuring site, which fluorescence components have wavelengths falling within a wavelength region of 700 nm±at most 70 nm and at least containing 700 nm to 710 nm, and
v) fluorescence information displaying means for displaying information in accordance with the light intensity B and a ratio between the light intensity, which has been detected by the at least one selected light intensity detecting means, and the light intensity w.

11. An apparatus as defined in claim 9 or 10 wherein the light intensity detecting means comprises an image sensor for two-dimensionally detecting the fluorescence produced by the measuring site and forming a fluorescence image, and wavelength selecting means for selecting the fluorescence components of the fluorescence produced by the measuring site, which fluorescence components have wavelengths falling within a desired wavelength region.

12. An apparatus as defined in claim 9 or 10 wherein the light intensity detecting means is provided with fluorescence acquiring means for acquiring the fluorescence, which is produced by a single point at a site in the living body.

13. An apparatus as defined in claim 9 or 10 wherein the excitation light has wavelengths falling within the range of 380 nm to 420 nm.

14. An apparatus as defined in claim 9 or 10 wherein the excitation light irradiating means is a GaN type of semiconductor laser.

\* \* \* \* \*